US012806156B2

(12) United States Patent
Nayani et al.

(10) Patent No.: US 12,806,156 B2
(45) Date of Patent: Nov. 24, 2026

(54) PHENYLEPHRINE PREMIX FORMULATIONS AND USES THEREOF

(71) Applicants: Baxter International, Inc., Deerfield, IL (US); Baxter Healthcare SA, Glattpark (CH)

(72) Inventors: Anil Kanjibhai Nayani, Ahmedabad (IN); Prahlad Pragallapati, Ahmedabad (IN); Pankajkumar Ramabhai Patel, Ahmedabad (IN)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 18/146,866

(22) Filed: Dec. 27, 2022

(65) Prior Publication Data

US 2023/0201140 A1 Jun. 29, 2023

(51) Int. Cl.

| | |
|---|---|
| ***A61K 31/137*** | (2006.01) |
| ***A61K 9/08*** | (2006.01) |
| ***A61K 47/02*** | (2006.01) |
| ***A61K 47/12*** | (2006.01) |

(52) U.S. Cl.

CPC .............. *A61K 31/137* (2013.01); *A61K 9/08* (2013.01); *A61K 47/02* (2013.01); *A61K 47/12* (2013.01)

(58) Field of Classification Search

CPC ...... A61K 47/02; A61K 47/12; A61K 31/137; A61K 9/08; A61K 9/0019; A61K 31/167

See application file for complete search history.

(56) References Cited

U.S. PATENT DOCUMENTS

| | | | | |
|---|---|---|---|---|
| 11,213,480 | B1 * | 1/2022 | McAnany | A61K 47/12 |
| 2007/0249727 | A1 * | 10/2007 | Martin | A61P 11/02 514/653 |
| 2015/0342928 | A1 | 12/2015 | Demopulos et al. | |
| 2020/0268746 | A1 | 8/2020 | Schmeichel et al. | |
| 2021/0228507 | A1 * | 7/2021 | Puri | A61K 31/137 |
| 2021/0308124 | A1 | 10/2021 | Torralva | |
| 2022/0257537 | A1 | 8/2022 | Caronzolo et al. | |

OTHER PUBLICATIONS

Cantrell Drug Company, Phenylephrine HCI. (Year: 2015).*

Kim et al. Development of photo-sensitive aluminum electrode materials in PDPs, IMID, p. 269-271. (Year: 2009).*

Biorphen—phenylephrine hydrochloride injection, solution, 0.1 mg/mL pr 10 mg/mL, Eton Pharmaceuticals, Inc., 19 pages (Oct. 2019).

Cantrell Drug Company, "Drug label Phenylephrine HCI—phenylephrine hydrochloride injection, solution", Jan. 2015. Retrieved from the Internet: <URL: https://fda.report/DailyMed/c68d7ecd-9c1d-48eO-bcf8-cb24996c8a30>.

Phenylephrine 50 micrograms/ml, Solution for Injection in Pre-filled Syringe, Laboratoire Aguettant, Jan. 7, 2015. Retrieved from the Internet: <URL: https://www.medicines.org.uk/emc/product/1970/smpc#gref>. Entire document in FR with EN machine translation.

Prescribing Information Phenylephrine Hydrochloride Injection, 500 mcg/10mL, Vasopressor Intravenous (iv), BioSyent Pharma Inc., 2 pages (May 4, 2016).

Phenylephrine HCI Injection, USP 10mg/mL 1mL Vial, HF Acquisition Co LLC, manufactured by West-Ward Pharmaceuticals, 15 pages (Jun. 2020).

Vazculep (phenylephrine hydrochloride) Injection for intravenous use 10 mg/mL, Éclat Pharmaceuticals, 10 pages (Jun. 2014).

Vazculep—phenylephrine hydrochloride injection, 10 mg/mL, Exela Phrama Sciences, LLC, 21 pages (Mar. 2021).

World Intellectual Property Organization, International Search Report and Written Opinion for PCT/US2022/082426, mailed Mar. 21, 2023.

Huang, Drug Development & Delivery, May 2021. Formulation Forum—Considerations in Formulation Development of Injectable Solutions. Retrieved from the Internet: <URL: https://drug-dev.com/formulation-forum-considerations-in-formulation-development-of-injectable-solutions/>.

World Intellectual Property Organization, International Preliminary Report for Patentability for PCT/US2022/082426, mailed Aug. 20, 2024.

Kiser TH, Oldland AR, Fish DN. "Stability of phenylephrine hydrochloride injection in polypropylene syringes." Am J Health-Syst Pharm. 2007;64:1092-1095.

Gupta VD. "Chemical stability of phenylephrine hydrochloride after reconstitution in 0.9% sodium chloride injection for infusion." Int J Pharm Compd. 2004;8(2):153-155.

Jansen JJ, Oldland AR, Kiser TH. "Evaluation of phenylephrine stability in polyvinyl chloride bags." Hosp Pharm. 2014;49(5):455-457.

* cited by examiner

*Primary Examiner* — Kamal A Saeed
*Assistant Examiner* — Meghan C Heasley
(74) *Attorney, Agent, or Firm* — Womble Bond Dickinson (US) LLP

(57) ABSTRACT

The present disclosure is directed to a pharmaceutical premix phenylephrine formulation comprising phenylephrine hydrochloride and a salt, e.g., sodium chloride, where the formulation has a pH from about 3.0 to 6.5. Also presented is a system containing an oxygen scavenger, a photosensitive overpouch, and a pharmaceutical premix phenylephrine formulation. Methods of treating hypotension, e.g., resulting primarily from vasodilation, in such settings as septic shock or anaesthesia, in a human subject are also described.

35 Claims, No Drawings

PHENYLEPHRINE PREMIX FORMULATIONS AND USES THEREOF

RELATED APPLICATIONS

This application claims priority to Indian application no. 202141061521, filed on Dec. 29, 2021. The contents of the foregoing application are hereby incorporated by reference herein.

TECHNICAL FIELD

The present disclosure generally relates to stable liquid phenylephrine hydrochloride pharmaceutical premix formulations and uses thereof.

BACKGROUND

Phenylephrine hydrochloride (HCl) is an al-adrenergic receptor agonist with potent vasoconstrictor properties, possessing both direct and indirect sympathomimetic effects. Phenylephrine hydrochloride has multiple medical uses, including as a decongestant, a pupil dilator, and to increase blood pressure. While phenylephrine hydrochloride may be delivered orally, e.g., to treat congestion, it can also be administered via intravenous (IV), subcutaneous, or intramuscular routes. Phenylephrine hydrochloride, administered by injection or IV infusion, is used for the treatment of hypotensive states, e.g. circulatory failure, during spinal anesthesia, and to counteract drug-induced hypotension.

Typically. IV solutions of phenylephrine hydrochloride are diluted prior to use, as they are commonly formulated in amounts useful for subcutaneous or intramuscular administration to the patient. There remains a need for a stable, premix IV formulation of phenylephrine hydrochloride which can be used without preparation. e.g., dilution, prior to being administered to a patient.

SUMMARY

Typically, phenylephrine hydrochloride (HCl) for intravenous (IV) delivery is provided in a vial and must be diluted prior to administration to a patient. This requisite dilution is inconvenient, time consuming, and can be subject to errors and product contamination. Therefore, a need exists for an improved phenylephrine formulation that is stable and contains an appropriate premix amount of phenylephrine hydrochloride (HCl) such that the formulation is ready for delivery to the patient. Described herein are phenylephrine HCl formulations that are premixed and ready for infusion to the patient.

Provided herein is a pharmaceutical premix formulation comprising from about 0.05 milligrams per milliliter (mg/ml) to about 0.5 mg/ml phenylephrine hydrochloride and a salt, wherein the formulation is an aqueous, premix formulation and has a pH from about 3.0 to about 6.5.

In one embodiment, the pharmaceutical premix formulation comprises from about 0.08 mg/ml to about 0.4 mg/mi phenylephrine hydrochloride. In another embodiment, the pharmaceutical premix formulation comprises about 0.08 mg/ml phenylephrine hydrochloride. In still another embodiment, the pharmaceutical premix formulation comprises about 0.1 mg/ml phenylephrine hydrochloride. In still another embodiment, the pharmaceutical premix formulation comprises about 0.16 mg/ml phenylephrine hydrochloride. In one embodiment, the pharmaceutical premix formulation comprises about 0.2 mg/ml phenylephrine hydrochloride. In one embodiment, the pharmaceutical premix formulation comprises about 0.4 mg/ml phenylephrine hydrochloride.

In one embodiment, the salt in the pharmaceutical premix formulation disclosed herein is sodium chloride. In one embodiment, the pharmaceutical premix formulation comprises from about 8.5 mg/ml to about 9.5 mg/ml sodium chloride. In one embodiment, the pharmaceutical premix formulation comprises from about 8.7 mg/ml to about 9.3 mg/ml sodium chloride. In one embodiment, the pharmaceutical premix formulation comprises about 9 mg/ml sodium chloride. In still another embodiment, the pharmaceutical premix formulation comprises 0.9% sodium chloride.

In one embodiment, the pharmaceutical premix formulation disclosed herein has a pH from about 3.5 to about 6.0.

In one embodiment, the pharmaceutical premix formulation disclosed herein further comprises sodium citrate dihydrate and citric acid monohydrate. In one embodiment, the pharmaceutical premix formulation comprises from about 0.05 to about 1.1 mg/ml sodium citrate dihydrate. In one embodiment, the pharmaceutical premix formulation comprises from about 0.01 to about 0.03 mg/ml citric acid monohydrate. In one embodiment, the pharmaceutical premix formulation comprises about 0.08 mg/ml sodium citrate dihydrate. In one embodiment, the pharmaceutical premix formulation comprises about 0.02 mg/mi citric acid monohydrate.

In a further embodiment, the pharmaceutical premix formulation disclosed herein is sulfite free.

Also provided herein is a pharmaceutical premix formulation consisting essentially of phenylephrine hydrochloride, sodium chloride, sodium citrate dihydrate, and citric acid monohydrate, wherein the pharmaceutical premix formulation is an aqueous, premix formulation and has a pH from about 3.0 to about 6.5. In one embodiment, the pharmaceutical premix formulation comprises from about 0.05 mg/ml to about 0.5 mg/ml phenylephrine hydrochloride. In another embodiment, the pharmaceutical premix formulation comprises from about 8.4 mg/mi to about 9.4 mg/ml sodium chloride. In yet another embodiment, the pharmaceutical premix formulation comprises from about 0.05 to about 1.1 mg/ml sodium citrate dihydrate and/or from about 0.01 to about 0.03 mg/ml citric acid monohydrate.

Also provided herein is a pharmaceutical premix formulation consisting essentially of about 0.08 mg/ml phenylephrine hydrochloride, about 0.9% sodium chloride, about 0.08 mg/ml sodium citrate dihydrate, and about 0.02 mg/ml citric acid monohydrate, wherein the pharmaceutical premix formulation is an aqueous, premix formulation and has a pH from about 3.0 to about 6.5.

Further provided herein is a pharmaceutical premix formulation consisting essentially of about 0.1 mg/ml phenylephrine hydrochloride, about 0.9% sodium chloride, about 0.08 mg/ml sodium citrate dihydrate, and about 0.02 mg/ml citric acid monohydrate, wherein the pharmaceutical premix formulation is an aqueous, premix formulation and has a pH from about 3.0 to about 6.5.

Also provided is a pharmaceutical premix formulation consisting essentially of about 0.16 mg/ml phenylephrine hydrochloride, about 0.9% sodium chloride, about 0.08 mg/ml sodium citrate dihydrate, and about 0.02 mg/ml citric acid monohydrate, wherein the pharmaceutical premix formulation is an aqueous, premix formulation and has a pH from about 3.0 to about 6.5.

In a further embodiment is provided a pharmaceutical premix formulation consisting essentially of about 0.2 mg/ml phenylephrine hydrochloride, about 0.9% sodium chloride, about 0.08 mg/ml sodium citrate dihydrate, and about 0.02 mg/ml citric acid monohydrate, wherein the pharmaceutical premix formulation is an aqueous, premix formulation and has a pH from about 3.0 to about 6.5.

Provided herein is a pharmaceutical premix formulation consisting essentially of about 0.4 mg/ml phenylephrine hydrochloride, about 0.9% sodium chloride, about 0.08 mg/ml sodium citrate dihydrate, and about 0.02 mg/ml citric acid monohydrate, wherein the pharmaceutical premix formulation is an aqueous, premix formulation and has a pH from about 3.0 to about 6.5.

In one embodiment, the pharmaceutical premix formulation is stable at 25 degrees Celsius for at least 6 months.

Also provided herein is a flexible container comprising the pharmaceutical premix formulation disclosed herein. In one embodiment, the flexible container is polypropylene (PP), polyamide (PA), or polyethylene (PE), or a combination thereof. In one embodiment, the flexible container has a volume of about 100 mL or about 250 mL.

Also provided herein is a system comprising an oxygen scavenger and a pharmaceutical premix formulation as disclosed herein. In one embodiment, the system further comprises an overpouch which is photosensitive. In one embodiment, the system consists essentially of an oxygen scavenger, a photosensitive overpouch, and a pharmaceutical premix formulation. In one embodiment, the oxygen scavenger is in a polyethylene container. In one embodiment, the oxygen scavenger comprises micronized iron. In one embodiment, the oxygen absorber is located in between a container comprising the pharmaceutical premix formulation and the overpouch.

Also provided herein is a method of treating hypotension in a human subject in need thereof, the method comprising intravenously administering to the human subject in need thereof, a pharmaceutical premix formulation as described herein, wherein the pharmaceutical premix formulation is not diluted prior to intravenous administration to the human subject. In one embodiment, the human subject is undergoing anesthesia and/or has septic shock.

In one embodiment, the pharmaceutical premix formulation is administered as an intravenous bolus. In another embodiment, the pharmaceutical premix formulation is administered as a continuous intravenous infusion.

DETAILED DESCRIPTION

The present disclosure is generally directed to a ready to use pharmaceutical premix formulation comprising a phenylephrine hydrochloride (HCl) and to a process for the preparation thereof, as well as uses. The pharmaceutical premix formulations are advantageous in minimizing the potential for medication errors and to make administration of the phenylephrine solution easier for medical professionals in an infusion regimen. This is important given the types of indications intravenous (IV) phenylephrine is used for, including but not limited to, septic shock and emergency anesthesia procedures.

Disclosed herein are ready to use premix formulations of phenylephrine hydrochloride which are stable at room temperature. The premix formulations may be contained within a container closure system, e.g., 250 mL VIAFLO container closure system. The premix formulations described herein are diluted forms of phenylephrine hydrochloride, e.g., 80 to 400 μg/mL, which can be used for intravenous bolus or as a continuous infusion depending on the dosage requirement.

More specifically, the present disclosure is directed to pharmaceutical premix formulations comprising from about 0.05 mg/ml to about 0.5 mg/ml phenylephrine hydrochloride, wherein the formulation is aqueous and has a pH in a range from about 3.0 to 6.5. The liquid phenylephrine premix pharmaceutical formulations as described herein are ready for administration without the need for dilution to achieve a certain concentration suitable for administration to a human patient. The formulations of the disclosure can be administered to a human patient in need thereof intravenously. e.g., as either a bolus intravenous dose or by continuous intravenous infusion. The liquid phenylephrine premix pharmaceutical formulations described herein may be terminally sterilized or aseptically filled into a container, preferably a flexible container, such as VIAFLO. Further, the premix formulations may be used in a system with an oxygen scavenger and/or a photosensitive overpouch.

Definitions

With respect to the terms used in this disclosure, the following definitions are provided. This application will use the following terms as defined below unless the context of the text in which the term appears requires a different meaning.

The phrase "consists essentially of" as used herein, refers to specified materials or steps where anything unspecified that does not materially affect the basic characteristics of the specified materials or steps may be included with the materials or steps. In reference to a premix formulation, "consisting essentially thereof," means that the formulation necessarily includes the listed ingredients and is open to unlisted ingredients that do not materially affect the basic nature of the premix formulation, e.g., liquid, sterile, or the activity of the active ingredient, i.e., phenylephrine HCl.

As used herein, an "effective amount" is an amount of a drug (e.g., phenylephrine hydrochloride) that provides a nutritional, physiological, or medical benefit to the individual. In one embodiment, an effective amount of phenylephrine HCl is an amount that provides for the desired medical purpose, e.g., increasing blood pressure in adults with clinically important hypotension resulting primarily from vasodilation, in such settings as septic shock or anesthesia.

A "patient". "subject" or "individual", used interchangeably herein, is a mammal, preferably a human.

The term "pharmaceutical formulation" refers to a preparation, e.g., a liquid solution, which is in such form as to permit the biological activity of an active ingredient, e.g., phenylephrine HCl, contained therein to be effective, and which contains no additional components which are unacceptably toxic to a subject to which the formulation would be administered.

The term "aqueous" when used in reference to a formulation refers to a liquid formulation in which the solvent is water (e.g., water for injection (WFI)).

The term "pharmaceutically acceptable" as used herein refers to substances that do not cause substantial adverse allergic or immunological reactions when administered to a subject.

As used herein, the term "premix" refers to a ready to use, liquid solution suitable for direct administration to patients, including intravenous (IV) infusion, without requiring dilution. "Premix" indicates the formulation is already mixed and is suitable for administration to a human patient. Preferably, the premix solution is supplied as a sterile solution, and is stable over its shelf life, as described herein. A formulation that requires dilution prior to administration to a subject is not a premix formulation.

A "stable" formulation is one in which the active ingredient therein, e.g. phenylephrine HCl, essentially retains its physical and chemical stability, therefore its biological activity, upon storage.

As used herein, the term "sterile" is understood to mean free from any bacteria or other living microorganisms.

The terms "substantially no," "essentially free" or "substantially free" as used in reference to a particular component means that any of the component present constitutes less than about 3.0% by weight, such as less than about 2.0% by weight, less than about 1.0% by weight, preferably less than about 0.5% by weight or, more preferably, less than about 0.1% by weight.

As used herein, the term "about" means +/−10% of any recited value, or in an alternative embodiment, +/−5% of any recited value. As used herein, this term modifies any recited value, range of values, or endpoints of one or more ranges.

Phenylephrine Premix Pharmaceutical Formulations, Systems, and Uses Thereof

A pharmaceutical premix formulation disclosed herein provides multiple advantages over the art. Phenylephrine hydrochloride (HCl) is mainly administered by intramuscular, subcutaneous & intravenous modes. Generally, phenylephrine HCl injection is available as a concentrated solution which needs to be diluted to achieve the desired concentration before administration to a human patient as an intravenous bolus or continuous intravenous infusion. The concentrated phenylephrine formulation, for example, generally needs to be diluted with 0.9% sodium chloride or 5% dextrose in water. Once the diluted solutions are prepared, they are typically not held for more than 4 hours at room temperature or 24 hours under refrigerated conditions.

Disclosed herein is a premix pharmaceutical formulation having an amount of phenylephrine HCl that is suitable for administering to a human patient without first diluting the formulation. A pharmaceutical premix formulation described herein has a phenylephrine HCl concentration suitable to administer a desired effective dose to a human patient—thus improving efficiency and also minimizing the potential for error that may result from the dilution process. Generally, the pharmaceutical premix formulation described herein has a low concentration of phenylephrine HCl, e.g., less than 0.5 mg/ml (e.g., 0.08 to 0.4 mg/ml) which does not require dilution prior to be administered to a patient. Phenylephrine Hydrochloride is an alpha-1 adrenergic receptor agonist indicated for increasing blood pressure in adults with clinically important hypotension resulting primarily from vasodilation, in such settings as septic shock or anaesthesia.

The pharmaceutical premix formulations described herein include phenylephrine. Phenylephrine is an al-adrenergic receptor agonist with potent vasoconstrictor properties. A pharmaceutically acceptable salt of phenylephrine is phenylephrine hydrochloride. As used herein, the terms phenylephrine and phenylephrine hydrochloride (HCl) are used interchangeably in reference to a formulation and refer to 3-[(1R)-1-hydroxy-2-(methylamino)ethyl]phenol hydrochloride. Phenylephrine HCl has a chemical formula $C_9H_{13}NO_2 \cdot HCl$ and a structural formula as follows:

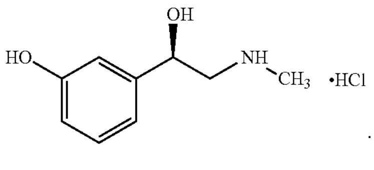

.

Presented herein are premix, aqueous pharmaceutical formulations which are stable and contain phenylephrine HCl. Notably, the premix formulations described herein do not need to be diluted prior to administration to a patient. Further, they are stable at room temperature.

Described herein is a pharmaceutical premix formulation comprising from about 0.05 mg/ml to about 0.5 mg/ml phenylephrine HCl and a salt, wherein the formulation is an aqueous, premix formulation and has a pH from about 3.0 to about 6.5.

In one embodiment, the salt used in the pharmaceutical premix formulation comprising phenylephrine HCl is sodium chloride. In one embodiment, the pharmaceutical premix formulation disclosed herein comprises phenylephrine HCl and from about 8 to about 9.5 mg/ml of sodium chloride. In other embodiments, the pharmaceutical premix formulation disclosed herein comprises phenylephrine HCl and from about 8.5 to about 9.5 mg/ml of sodium chloride. In other embodiments, the pharmaceutical premix formulation disclosed herein comprises phenylephrine HCl and from about 8.7 to about 9.3 mg/mi sodium chloride. In one embodiment, the pharmaceutical premix formulation disclosed herein comprises phenylephrine HCl and about 9.0 mg/ml sodium chloride.

The amount of phenylephrine or the amount of salt. e.g., sodium chloride, in the pharmaceutical premix formulation may be described in terms of percentage by weight per volume (w/v), e.g., 0.9% sodium chloride, or by concentration in the pharmaceutical premix formulation, e.g., 9.0 mg/ml sodium chloride. Concentrations of components of the formulation may also be expressed in terms of molarity (e.g., M or mM); the number of moles or millimoles per liter, respectively).

In one embodiment, the amount of salt, e.g., sodium chloride, is described in terms of the w/v % of the liquid solution. For example, the pharmaceutical premix formulation may contain from about 0.7% to about 1.1% sodium chloride or about 0.9% sodium chloride.

The osmolality of the pharmaceutical premix formulation comprising phenylephrine should be suitable for administration, e.g., intravenous, to a human patient. For example, the formulation can have an osmolality from about 270 to about 330 mOsm/kg.

One feature of the pharmaceutical premix formulation described herein is the relatively low concentration of phenylephrine HCl. Specifically, the concentration is such that dilution of the phenylephrine pharmaceutical premix formulation is not required (i.e., the ready-to-use, stable pharmaceutical premix formulation described herein does not require mixing or diluting prior to delivery to a human patient). The ready-to-use, stable, liquid premix formulation has a phenylephrine HCl concentration ranging from about 0.05 to 0.5 mg/ml, such as 0.05, 0.1, 0.15, 0.2, 0.25, 0.3, 0.35, 0.4, 0.45, 0.5 mg/ml, or from about 0.08 to about 0.4 mg/ml, of phenylephrine. In one embodiment, the pharmaceutical premix formulation comprises about 0.08 mg/ml phenylephrine. In one embodiment, the pharmaceutical premix formulation comprises about 0.1 mg/ml phenylephrine. In one embodiment, the pharmaceutical premix formulation comprises about 0.16 mg/ml phenylephrine. In one embodiment, the pharmaceutical premix formulation comprises about 0.2 mg/ml phenylephrine HCl. In other embodiments, the concentration of phenylephrine is about 0.4 mg/ml.

In one embodiment, provided herein is a pharmaceutical premix formulation comprising about 0.08 mg/ml phenylephrine hydrochloride and 0.9% sodium chloride, wherein the pharmaceutical premix formulation is an aqueous, premix formulation and has a pH from about 3.0 to about 6.5.

In one embodiment, provided herein is a pharmaceutical premix formulation comprising about 0.1 mg/ml phenylephrine hydrochloride and 0.9% sodium chloride, wherein the pharmaceutical premix formulation is an aqueous, premix formulation and has a pH from about 3.0 to about 6.5.

In one embodiment, provided herein is a pharmaceutical premix formulation comprising about 0.16 mg/ml phenylephrine hydrochloride and 0.9% sodium chloride, wherein the pharmaceutical premix formulation is an aqueous, premix formulation and has a pH from about 3.0 to about 6.5.

In one embodiment, provided herein is a pharmaceutical premix formulation comprising about 0.2 mg/ml phenylephrine hydrochloride and 0.9% sodium chloride, wherein the pharmaceutical premix formulation is an aqueous, premix formulation and has a pH from about 3.0 to about 6.5.

In one embodiment, provided herein is a pharmaceutical premix formulation comprising about 0.4 mg/ml phenylephrine hydrochloride and 0.9% sodium chloride, wherein the pharmaceutical premix formulation is an aqueous, premix formulation and has a pH from about 3.0 to about 6.5.

In certain embodiments, the pharmaceutical premix formulation comprises phenylephrine HCl, sodium chloride, sodium citrate dihydrate, and citric acid monohydrate. Sodium citrate dihydrate and citric acid monohydrate act as buffers in the premix formulation. For example, the pharmaceutical premix formulation may contain from about 0.05 to about 1.1 mg/ml sodium citrate dihydrate and/or from about 0.01 to about 0.03 mg/ml citric acid monohydrate. In certain embodiments, the pharmaceutical premix formulation contains about 0.08 mg/ml sodium citrate dihydrate and about 0.02 mg/ml citric acid monohydrate. In certain embodiments, the pharmaceutical premix formulation is free of acetate buffer.

Pharmaceutical premix formulations described herein are sulfite free but are also stable at room temperature and ready to use. Thus, in one embodiment, a pharmaceutical premix formulation described herein contains phenylephrine HCl but does not contain a sulfite, e.g., sodium metabisulfite (SMBS). Surprisingly, it was found according to the present disclosure that a sulfite such as SMBS is not needed for stability of the active ingredient phenylephrine HCl.

In one embodiment, provided herein is a pharmaceutical premix formulation comprising about 0.08 mg/ml phenylephrine hydrochloride and 0.9% sodium chloride, wherein the pharmaceutical premix formulation is an aqueous, premix formulation and has a pH from about 3.0 to about 6.5, and wherein the premix formulation is essentially free of a sulfite, such as SMBS.

In one embodiment, provided herein is a pharmaceutical premix formulation comprising about 0.1 mg/ml phenylephrine hydrochloride and 0.9% sodium chloride, wherein the pharmaceutical premix formulation is an aqueous, premix formulation and has a pH from about 3.0 to about 6.5, and wherein the premix formulation is essentially free of a sulfite, such as SMBS.

In one embodiment, provided herein is a pharmaceutical premix formulation comprising about 0.16 mg/ml phenylephrine hydrochloride and 0.9% sodium chloride, wherein the pharmaceutical premix formulation is an aqueous, premix formulation and has a pH from about 3.0 to about 6.5, and wherein the premix formulation is essentially free of a sulfite, such as SMBS.

In one embodiment, provided herein is a pharmaceutical premix formulation comprising about 0.2 mg/ml phenylephrine hydrochloride and 0.9% sodium chloride, wherein the pharmaceutical premix formulation is an aqueous, premix formulation and has a pH from about 3.0 to about 6.5, and wherein the premix formulation is essentially free of a sulfite, such as SMBS.

In one embodiment, provided herein is a pharmaceutical premix formulation comprising about 0.4 mg/ml phenylephrine hydrochloride and 0.9% sodium chloride, wherein the pharmaceutical premix formulation is an aqueous, premix formulation and has a pH from about 3.0 to about 6.5, and wherein the premix formulation is essentially free of a sulfite, such as SMBS.

The pH of the pharmaceutical premix formulation described herein is a pH that maintains the stability of phenylephrine HCl. The pH of the pharmaceutical premix formulation is in the range of about 3.0 to about 6.5, such as, for example, about 3.0, about 3.1, about 3.2, about 3.3, about 3.4, about 3.5, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, and about 6.5 (ranges including the numbers described herein are also contemplated, e.g., 3.3 to 6.2). In certain embodiments, the pharmaceutical premix formulation has a pH of about 3.5 to about 6.0.

The pH of the solution may be adjusted by use of a pH adjusting agent, and optionally, if needed a buffer may be used to maintain the pH in the said range. The pH adjusting agent that may be used include, but are not limited to, sodium hydroxide, potassium hydroxide, hydrochloric acid, sulphuric acid, acetic acid, sodium acetate, tartaric acid, and the like, and mixtures thereof. In one embodiment, the pH adjusting agent is sodium hydroxide, hydrochloric acid, or a combination thereof.

In some embodiments, the pharmaceutical premix formulation provided herein contains about 0.08 mg/ml phenylephrine hydrochloride, about 9.0 mg/ml of sodium chloride, 0.08 mg sodium citrate dihydrate, and about 0.02 mg citric acid monohydrate in water for injection.

In some embodiments, the pharmaceutical premix formulation provided herein contains about 0.1 mg/ml phenylephrine hydrochloride, about 9.0 mg/ml of sodium chloride, about 0.08 mg sodium citrate dihydrate, and about 0.02 mg citric acid monohydrate in water for injection.

In some embodiments, the pharmaceutical premix formulation provided herein contains about 0.16 mg/ml phenylephrine hydrochloride, about 9.0 mg/ml of sodium chloride, about 0.08 mg sodium citrate dihydrate, and about 0.02 mg citric acid monohydrate in water for injection.

In some embodiments, the pharmaceutical premix formulation provided herein contains about 0.2 mg/ml phenylephrine hydrochloride, about 9.0 mg/ml of sodium chloride, about 0.08 mg sodium citrate dihydrate, and about 0.02 mg citric acid monohydrate in water for injection.

In some embodiments, the pharmaceutical premix formulation provided herein contains about 0.4 mg/ml phenylephrine hydrochloride, about 9.0 mg/ml of sodium chloride, about 0.08 mg sodium citrate dihydrate, and about 0.02 mg citric acid monohydrate in water for injection.

In some embodiments, the pharmaceutical premix formulation provided herein comprises from about 20 to about 100 mg of phenylephrine HCl at a concentration from about 0.08 mg/ml to about 0.4 mg/ml, from about 8.4 mg/ml to about 9.5 mg/ml sodium chloride, and has a pH from about 3.0 to about 6.5. In some embodiments, the pharmaceutical premix formulation provided herein comprises about 20 mg of phenylephrine HCl at a concentration of about 0.08 mg/ml phenylephrine HCl, from about 8.4 mg/ml to about 9.5 mg/ml sodium chloride, and has a pH from about 3.0 to about 6.5. In some embodiments, the pharmaceutical premix formulation provided herein comprises about 25 mg of phenylephrine HCl at a concentration of about 0.1 mg/ml phenylephrine HCl, from about 8.4 mg/ml to about 9.5 mg/ml sodium chloride, and has a pH from about 3.0 to about 6.5. In some embodiments, the pharmaceutical premix formulation provided herein comprises about 40 mg of phenylephrine HCl at a concentration of about 0.16 mg/ml phenylephrine HCl, from about 8.4 mg/ml to about 9.5 mg/ml sodium chloride, and has a pH from about 3.0 to about 6.5. In some embodiments, the pharmaceutical premix formulation provided herein comprises about 50 mg of phenylephrine HCl at a concentration of about 0.2 mg/mi phenylephrine HCl, from about 8.4 mg/ml to about 9.5 mg/ml sodium chloride, and has a pH about 3.0 to about 6.5. In some embodiments, the pharmaceutical premix formulation provided herein comprises about 100 mg of phenylephrine HCl at a concentration of about 0.4 mg/ml phenylephrine HCl, from about 8.4 mg/ml to about 9.5 mg/ml sodium chloride, and has a pH from about 3.0 to about 6.5.

The pharmaceutical premix formulation of the disclosure may be characterized according to stability, such as long-term stability to storage. For example, in some embodiments, the pharmaceutical premix formulation is stable for at least 3 months or at least 6 months of storage at about 25 degrees Celsius. For example, in some embodiments, the pharmaceutical premix formulation is stable for at least 3 months of storage at about 40 degrees Celsius. For example, in some embodiments, the pharmaceutical premix formulation is stable for 6 months of storage at about 40 degrees Celsius.

Stability may be measured by the level of degradant over time. Impurities may be formed via degradation of one or more components of the composition. Sources of degradation include, but are not limited to, oxidation, racemization, visible light, ultraviolet light, moisture, heat, changes in pH, and composition component interactions.

Stability of a pharmaceutical premix formulation can be determined by assaying the level of degradant(s) over a period of time. Examples of degradants of phenylephrine are phenylephrone and phenylephrine-citrate adduct. Preferably, minimal or non-detectable levels of degradant are found over a testing period. For example, a pharmaceutical premix formulation may be stable if it is essentially free of both phenylephrone and phenylephrine-citrate adduct following storage at 25 degrees Celsius over six months, where levels of the degradant are non-detectable. In one embodiment, a pharmaceutical premix formulation is stable if it contains an amount of phenylephrone and/or phenylephrine-citrate adduct within pharmaceutical permissible limits following storage at 25 degrees Celsius over six months.

Impurities can be as measured using techniques known in the art, such as HPLC/UV, ultra-performance liquid chromatography (UPLC), gas chromatography-mass spectrometry (GCMS), liquid chromatography-mass spectrometry (LCMS), or inductively coupled plasma mass spectroscopy (ICPMS).

In one embodiment, a pharmaceutical premix formulation comprises phenylephrine HCl and comprises a low level of phenylephrine related impurities. For example, a pharmaceutical premix formulation described herein may comprise a low level of the degradation product phenylephrone and/or phenylephrine-citrate adduct. In one embodiment, the pharmaceutical premix formulation contains less than about 1%, less than about 0.5%, or less than about 0.2% of phenylephrone and/or phenylephrine-citrate adduct as determined by HPLC/UV. In some embodiments, the amount of phenylephrone and/or phenylephrine-citrate adduct in the pharmaceutical premix formulation after a certain period of shelf life may be no more than about 9.5%, preferably no more than about 9%, more preferably no more than about 8.5%, more preferably no more than about 8%, more preferably no more than about 7.5%, more preferably no more than about 7%, more preferably no more than about 6.5%, more preferably no more than about 6%, more preferably no more than about 5.5%, more preferably no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and no more than about 0.5%, no more than about 0.4%, no more than about 0.3%, no more than about 0.2%, or no more than about 0.1%. In some embodiments, less than 10% of the phenylephrine in the pharmaceutical premix formulation is phenylephrone and/or phenylephrine-citrate adduct after at least six months of storage at about 25 degrees Celsius. In some embodiments, less than 10% of the phenylephrine in the pharmaceutical premix formulation is phenylephrone and/or phenylephrine-citrate adduct after at least three months of storage at about 40 degrees Celsius. Examples of storage conditions and respective levels of phenylephrine degradant (e.g., phenylephrone or phenylephrine-citrate adduct) are provided in the Examples below. The amounts recited in the tables in the Examples are also contemplated as being levels with respect to low levels of degradant which is representative of a stable phenylephrine premix formulation.

In some embodiments, the pharmaceutical premix formulation may have no more than about 1.3% of total degradation products after a certain period of shelf life, no more than about 1.2%, no more than about 1.1%, no more than about 1%, no more than about 0.9%, no more than about 0.85%, no more than about 0.8%, no more than about 0.75%, no more than about 0.7%, no more than about 0.65%, no more than about 0.6%, no more than about 0.55%, no more than about 0.5%, no more than about 0.45%, no more than about 0.4%, no more than about 0.35%, no more than about 0.3%, no more than about 0.25%, no more than about 0.2%, no more than about 0.15%, no more than about 0.1%, no more than about 0.09%, y no more than about 0.08%, no more than about 0.07%, no more than about 0.06%, or no more than about 0.05% total degradation products in the phenylephrine formulation.

The pharmaceutical premix formulation of the disclosure has long term stability, e.g., the formulation is stable for at least 6 months at 25 degrees Celsius. In other embodiments, the pharmaceutical premix formulation is stable for 3 months at 25 degrees Celsius.

Stability of the pharmaceutical premix formulation described herein is achieved without the use of a preservative. Thus, in certain embodiments, a pharmaceutical premix formulation of the disclosure comprising phenylephrine HCl is essentially free of a preservative. Examples of preservatives include, but are not limited to, sodium benzoate. EDTA, sorbic acid, and parabens. In certain embodiments, the pharmaceutical premix formulation is free of EDTA. e.g., is free of disodium EDTA.

In certain embodiments, the pharmaceutical premix formulation comprises about 0.05 mg/ml to about 0.5 mg/ml phenylephrine HCl, and about 8.4 to about 9.4 mg/ml sodium chloride. In one embodiment the formulation is an aqueous, premix pharmaceutical formulation and has a pH of about 3.0 to 6.5. Further, the formulation may be essentially free of a preservative.

A phenylephrine pharmaceutical premix formulation described herein may be confined within a flexible container, such as an intravenous bag. The volume capacity of the flexible container can range, for example, from about 50 mL to 1000 mL.

A flexible container, such as a bag, provides better control relative to a rigid container, providing enhanced safety. Flexible bags suitable as containers include those disclosed in US 2008/0249499, which is hereby incorporated by reference in its entirety. Other flexible bags may be used. Preferred flexible bag primary containers may be free of PVC (non-PVC), such as those disclosed in U.S. Pat. Nos. 5,849,843 and 5,998,019, which are hereby incorporated by reference in their entirety. Suitable flexible polymeric primary containers include but are not limited to GALAXY IV containers (Baxter International Inc.). VIAFLO containers (Baxter International Inc.), and INTRAVIA containers (Baxter International Inc.), in one embodiment, a flexible container used to house the premix phenylephrine formulation is a flexible plastic container fabricated from a multilayer sheeting composed of polypropylene (PP), polyamide (PA) and polyethylene (PE).

In certain embodiments, the volume capacity of each flexible container may range from about 50 ml to about 500 ml, such as for example 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440 or 450 ml, more preferably from about 50 ml to 250 ml. According to some embodiments, the flexible container (e.g., infusion bag) can accommodate a volume from about 100 ml to 250 ml of the pharmaceutical premix formulation, preferably about 250 ml. In certain embodiments, the volume of the flexible container is about 50 mL. In certain embodiments, the volume of the flexible container is about 100 mL. In certain embodiments, the volume of the flexible container is about 250 mL. In certain embodiments, the volume of the flexible container is about 500 mL. In certain embodiments, the volume of the flexible container is about 1000 mL. The flexible container, e.g., a plastic bag, may be suitable for intravenous infusion of the pharmaceutical premix formulation to a human subject. In some embodiments, the pharmaceutical premix formulation of phenylephrine filled in the flexible container comprises a concentration in the range of about 0.08 mg/mi to about 0.4 mg/ml of phenylephrine HCl. In one embodiment, the pharmaceutical premix formulation of phenylephrine HCl filled in the flexible container comprises a concentration of 0.08 mg/ml of phenylephrine HCl. In one embodiment, the pharmaceutical premix formulation of phenylephrine HCl filled in the flexible container comprises a concentration of 0.1 mg/ml of phenylephrine HCl. In one embodiment, the pharmaceutical premix formulation of phenylephrine filled in the flexible container comprises a concentration of 0.16 mg/ml of phenylephrine HCl. In another embodiment, the pharmaceutical premix formulation of phenylephrine HCl filled in the flexible container comprises a concentration 0.2 mg/ml of phenylephrine HCl. In yet another embodiment, the pharmaceutical premix formulation of phenylephrine HCl filled in the flexible container comprises a concentration of 0.4 mg/ml of phenylephrine HCl.

The material of the flexible container (e.g., IV bag) can be a plastic, e.g., the container may include polypropylene (PP), polyamide (PA), polyethylene (PE), and combinations thereof. In certain embodiments, the flexible container is a VIAFLO container, which is a bag composed of polyolefin/polyamide/polyethylene co-extruded plastic.

The premix formulation may be administered to a human patient intravenously via an infusion tube connected to the flexible container. A flexible container also provides better control over a rigid container for safety purposes. By avoiding dilution, where the sterile premix formulation is ready to use, contamination and/or medication error can be avoided. In some embodiments, the flexible container is part of an intravenous hook system such that the intravenous hook comprises the flexible container with the stable, ready-to-use pharmaceutical premix formulation of phenylephrine HCl.

In some embodiments, the flexible container is a flexible bag which is suitable for intravenous use, i.e, an IV bag. Such flexible bags may be formed by any of a number of methods, for example, by an exemplary form/fill/seal process where a sheet layer (or film) is aligned and then folded by a folding triangle. After that aligning and folding step, the film can be cut to allow the introduction of a port system between the two resulting facing films. The port system can then be automatically fed in place and welded between the two opposing faces of the folded film. By vertical welding, the bottom part of the bag is formed and a hanger hole is punched. The side of the bag is formed by horizontal welding, while the solution for infusion is fed into the formed flexible bag. The upper horizontal welding also can form the lower side of the next bag. Finally, each bag is separated from the other during a sealing/cutting process. Thus, the flexible bag may be formed of a single sheet layer of flexible material, folded and sealed along the peripheral edges. Examples of suitable flexible containers are described in US 2008/0249499 and US 2021/0275470, each of which is hereby incorporated by reference in their entirety with respect to the flexible containers described therein.

In other methods, two flexible sheets are joined at a top end and two side edges. i.e., when the two flexible sheets are placed in facing relationship they can be joined at their overlying/overlapping peripheral edges, while leaving an opening at a bottom end. The sealed top end and side edges, along with the open bottom end, are collectively referred to herein as the peripheral edges of the flexible bag. The top end includes a hanger aperture, which is preferably laterally offset from a central vertical axis of the flexible bag portion. The port system can then be fed in place and welded between the two opposing flexible sheets. Any other known method of bag manufacture, such as blow molding or vacuum forming, may also be used.

In one embodiment, a pharmaceutical premix formulation described herein may be contained in a flexible bag, such as a non-polyvinyl chloride (NPVC) flexible container. In some embodiments, the pharmaceutical premix formulation of phenylephrine HCl comprises a diluted form of phenylephrine HCl. e.g., 0.08 mg/ml, 0.1 mg/ml, 0.16 mg/ml, 0.2 mg/ml, or 0.4 mg/ml of phenylephrine HCl in 0.9% sodium chloride injection in non-polyvinyl chloride (NPVC) flexible container (e.g., 250 mL VIAFLO container closure system). In one embodiment, the pharmaceutical premix formulation of phenylephrine HCl comprises about 0.08 mg/ml in about 0.9% sodium chloride injection in NPVC flexible container. In one embodiment, the pharmaceutical premix formulation of phenylephrine HCl comprises about 0.1 mg/ml in about 0.9% sodium chloride injection in NPVC flexible container. In one embodiment, the pharmaceutical premix formulation of phenylephrine HCl comprises about 0.16 mg/ml in about 0.9% sodium chloride injection in NPVC flexible container. In one embodiment, the pharmaceutical premix formulation of phenylephrine HCl comprises about 0.2 mg/ml in about 0.9% sodium chloride injection in NPVC flexible container. In one embodiment, the pharmaceutical premix formulation of phenylephrine HCl comprises about 0.4 mg/ml in about 0.9% sodium chloride injection in NPVC flexible container.

The flexible container comprising the pharmaceutical premix formulation of phenylephrine HCl can be terminally sterilized without compromising with the stability of phenylephrine HCl. It was also found that phenylephrine solution when stored in a VIAFLO container remained stable upon long term storage with no signs of any visible particles and impurities also remained under pharmaceutically acceptable range.

In certain embodiments, provided herein is a room temperature stable, pharmaceutical premix formulation containing about 20 mg phenylephrine HCl at a concentration of 0.08 mg/ml, about 8.4 mg/ml to 9.4 mg/ml sodium chloride, about 0.08 mg sodium citrate dihydrate, and about 0.02 mg citric acid monohydrate, pH of about 3.0 to 6.5, which can be used for as a continuous infusion depending on dosage requirement. In some embodiments, provided herein is a room temperature stable, pharmaceutical premix formulation of about 25 mg phenylephrine HCl at a concentration of 0.1 mg/ml, about 8.4 mg/ml to 9.4 mg/ml sodium chloride (in a flexible container such as a 250 mL VIAFLO Container Closure System), about 0.08 mg sodium citrate dihydrate, and about 0.02 mg citric acid monohydrate, pH of about 3.0 to 6.5, which can be used for as a continuous infusion depending on dosage requirement. In some embodiments, provided herein is a room temperature stable, pharmaceutical premix formulation of about 40 mg phenylephrine HCl at a concentration of 0.16 mg/ml, about 8.4 mg/ml to 9.4 mg/ml sodium chloride (in a flexible container such as a 250 mL VIAFLO Container Closure System), about 0.08 mg sodium citrate dihydrate, and about 0.02 mg citric acid monohydrate, pH of about 3.0 to 6.5, which can be used for as a continuous infusion depending on dosage requirement. In some embodiments, provided herein is a room temperature stable, pharmaceutical premix formulation of about 50 mg phenylephrine HCl at a concentration of 0.2 mg/ml, about 8.4 mg/ml to 9.4 mg/ml sodium chloride (in a flexible container such as a 250 mL VIAFLO Container Closure System), about 0.08 mg sodium citrate dihydrate, and about 0.02 mg citric acid monohydrate. pH of about 3.0 to 6.5, which can be used for as a continuous infusion depending on dosage requirement. In some embodiments, provided herein is a room temperature stable, pharmaceutical premix formulation of about 100 mg phenylephrine HCl at a concentration of 0.4 mg/ml, about 8.4 mg/ml to 9.4 mg/ml sodium chloride (in a flexible container such as a 250 mL VIAFLO Container Closure System), about 0.08 mg sodium citrate dihydrate, and about 0.02 mg citric acid monohydrate, pH of about 3.0 to 6.5, which can be used for as a continuous infusion depending on dosage requirement.

In some embodiments, the phenylephrine HCl premix pharmaceutical formulation is contained within a primary container which is flexible. In one embodiment, a multilayer flexible sheet layer (or film) is used to manufacture the primary container. In one aspect according to this embodiment, the multilayer flexible sheet layer comprises a low-density polyethylene (PE) bottom (inside facing when assembled) layer such as Stamylex 1026F. a polypropylene (PP) top (outside facing when assembled) layer such as Bormed RD804CF or Bormed RE816CF, and a polyamide (PA) middle layer such as Grilon FG40NL Natural 6021. A composite PE bottom layer may also be used. A composite PP top layer may also be used. Adhesion between the PP and PA layers may be achieved by a tie layer comprising PP grafted with maleic anhydride such as Admer QF300E. Similarly, adhesion between the PA and PE layers may be achieved by a tie layer comprising PE grafted with maleic anhydride such as Yparex 8104E. In some embodiments, the flexible sheet does not comprise any cycloolefin polymers or cycloolefin copolymers.

The flexible sheet layer may have any suitable thickness, for example, between about 100 pm and about 250, pm, between about 125 pm and about 225, pm, and/or between about 150 pm and about 200 pm.

In certain embodiments, the phenylephrine HCl premix pharmaceutical formulation is contained in flexible plastic container which is fabricated from a multilayer sheeting comprising polypropylene, polyamide, and polyethylene. In one embodiment, the inner layer of the flexible container is made of polyethylene and is in contact with the phenylephrine HCl premix pharmaceutical formulation.

In one embodiment, the phenylephrine HCl premix pharmaceutical formulation is contained in a packaged, sealed container system. In some embodiments, the packaged, sealed container system comprises a primary container (as disclosed herein) including a ready-to-use pharmaceutical premix formulation of phenylephrine HCl therein, and further includes a secondary container. The primary container may be disposed within and enclosed by the secondary container. The secondary container may be an overpouch container. Overpouches are flexible containers that can be used as secondary containers in the packaged, sealed container system to store, protect, and transport the primary container containing the midazolam premix pharmaceutical formulation. Generally, overpouches are provided by a first flexible sheet layer, an opposing second flexible sheet layer, and a seal disposed along a common peripheral edge of the first and second flexible sheet layers. Preferably, the secondary overpouch container should be optically transparent to enable visual inspection of the primary container and any other contents within the overpouch. It is also desirable for the overpouch container to be capable of withstanding autoclaving or other terminal sterilization process without causing the primary container therein to shrink/wrinkle and without becoming discolored and/or adhered to the primary container The overpouch container may be an aluminum overpouch, a light absorbing polymeric overpouch, or a similar barrier structure. In one embodiment, the primary container is in communication with any other contents of the overpouch secondary container.

In one embodiment, the overpouch secondary container comprises a first flexible sheet layer comprising an amber transparent film and a second flexible sheet layer comprising an opaque aluminum laminated foil. The first flexible sheet layer of may be an amber transparent multilayer film comprising a PET (Polyethylene terephthalate)/PA/PP laminate to allow the contents within the secondary container, for example, any labeling on the primary container to be seen. The second flexible sheet layer may be an opaque laminated foil comprising a PET/PA/Aluminum foil/PP laminate. A seal is disposed along a common peripheral edge of the first and second flexible sheets.

In another embodiment, the overpouch secondary container comprises a first flexible single layer sheet layer comprising a polymeric blend of a high density polyethylene and a surface enhancing polymer, an opposing second flexible single layer sheet layer comprising a polymeric blend of a high density polyethylene and a surface enhancing polymer of an ethylene propylene diene terpolymer dispersed in a polyolefin matrix, and a seal disposed along a common peripheral edge of the first and second flexible sheets as disclosed in US 2006/0240204, which is hereby incorporated by reference in its entirety.

An oxygen scavenger may be disposed within and enclosed by the overpouch secondary container. The oxygen scavenger may comprise iron powder, iron oxide powder, or a mixture thereof, for example, micronized iron. Other known oxygen scavengers may also be used. The oxygen scavenger is primarily included to absorb small amounts of oxygen that permeate through the secondary container during the shelf life of the drug product. Accordingly, provided herein is also a system containing the pharmaceutical premix phenylephrine formulation described herein and an oxygen scavenger. The oxygen scavenger may be in the form of an oxygen absorbing sachet or a polyethylene container. The oxygen scavenger may, in certain embodiments, contain micronized iron, where, e.g., the iron in the oxygen absorbing sachet reacts with the oxygen in the headspace environment of the container to keep the oxygen content low within the system. Preferably the system is a container closure system, as the oxygen scavenger is not in the pharmaceutical premix phenylephrine formulation but rather outside of the container holding the pharmaceutical premix phenylephrine formulation, such that the oxygen scavenger acts to stabilize the pharmaceutical premix phenylephrine formulation by absorbing oxygen surrounding the container holding the formulation. As described in the examples below, the use of an oxygen scavenger improved stability of the formulation. Air (oxygen) can induce degradation via oxidation. Degradation can be minimized by filling the container as full as possible, thereby decreasing the headspace, or by replacing the headspace with nitrogen. Another option is to add an antioxidant to the formulation.

In one embodiment, a system comprises the pharmaceutical premix phenylephrine formulation, an oxygen scavenger and an overpouch. The oxygen scavenger may be located between the primary container and the overpouch. The oxygen scavenger may be in the form of a sachet made from polyethylene materials, which contains an oxygen absorbing mixture composed primarily from micronized iron. The aim of the oxygen scavenger (or absorber) is to absorb the oxygen ingress that occurs during the shelf life of phenylephrine.

Thus, despite the primary and secondary containers being sealed, the fluid contents of the primary container may be considered to be in fluid communication with the contents of the secondary container, including the oxygen scavenger. Thus, the oxygen scavenger can be considered to be in fluid communication with the formulation of the primary container.

The system described herein may also contain a component which is photosensitive and prevents light from contacting the pharmaceutical premix phenylephrine formulation. The effects of light can be minimized by packaging products (or providing a system) in light-resistant containers. For example, the system may contain a pouch which goes over the pharmaceutical premix phenylephrine formulation to prevent light from contacting the formulation. The overpouch may be made of aluminum foil and/or an amber plastic overwrap.

Thus, in certain embodiments, the pharmaceutical premix phenylephrine formulations can be in a system containing a flexible container containing the pharmaceutical premix phenylephrine formulation, an oxygen scavenger, and a photosensitive overpouch.

The premix formulation may be administered to a human patient intravenously via an infusion tube connected to the flexible container. In some embodiments, the flexible container is part of an intravenous hook system such that the intravenous hook comprises the flexible container with the stable, ready-to-use pharmaceutical premix formulation of phenylephrine HCl.

The premix formulations and the flexible container disclosed herein provide advantages over those other phenylephrine formulations known in the art. For example, a premix pharmaceutical formulation, like those disclosed herein, provides a certain dose amount (e.g., an IV bolus/Infusion) that is readily available to the patient without a need to first dilute the phenylephrine formulation. By providing a premix pharmaceutical formulation, which does not require dilution, the risk of contamination and compounding, or medication error associated therewith, is essentially eliminated. Furthermore, the flexible container of the present disclosure provides a means of direct intravenous administration of the sterile, stable formulation of phenylephrine HCl or a pharmaceutically acceptable salt thereof, to the patient through the infusion container, using the outlet port. Further, the formulation disclosed herein reduces time needed by medical experts to dilute and prepare phenylephrine for administration, and also reduces medical waste.

Importantly, the formulation described herein, which can be contained in a flexible container such as a plastic bag suitable for intravenous infusion, are ready to use for delivery of the phenylephrine HCl to the patient, i.e., there is no need to dilute the phenylephrine HCl and the premix formulation contained within the flexible container can be administered to the patient without a mixing and/or dilution step. In one embodiment, the system described herein (i.e., premix formulation in a flexible container, such as a VIAFLO plastic bag), provides improved safety for the patient by providing better control in contrast to rigid containers used to mix and dilute phenylephrine HCl to achieve a suitable concentration for administering an accurate dose.

In some aspects, there are provided methods of using the stable, premix pharmaceutical of phenylephrine HCl. Disclosed herein are methods of treating a human subject having a septic shock associated hypotension or anesthesia. In certain embodiments, the premix pharmaceutical formulation of phenylephrine HCl is administered to a human subject having a septic shock associated hypotension, wherein administration of the formulation reduces, alleviates or eliminates the septic shock associated with hypotension or anesthesia.

Phenylephrine HCl is indicated for increasing blood pressure in adults with clinically important hypotension resulting primarily from vasodilation, in such settings as septic shock or anesthesia. The dosing recommendations for hypotension during anesthesia is initial dose of 40 to 100 μg administered by intravenous bolus. Additional boluses may be administered every 1-2 minutes as needed, not to exceed a total dosage of 200 μg. If blood pressure is below the target goal, a continuous intravenous infusion is started with an infusion rate of 10 to 35 μg/minute, not to exceed 200

μg/minute. For bolus intravenous or for continuous intravenous administration, a medical professional typically has to prepare a diluted product solution with 5% dextrose injection, USP or 0.9% sodium chloride injection, USP. Once the diluted solution is prepared, it is typically not held for more than 4 hours at room temperature or for more than 24 hours under refrigerated conditions. Dosage is adjusted according to the blood pressure goal.

In certain embodiments, the pharmaceutical premix formulation described herein has a concentration of about 80 μg/mL, about 100 μg/mL, about 160 μg/mL, about 200 μg/mL, or about 400 μg/mL of phenylephrine hydrochloride. The total mg amount of phenylephrine HCl in a pharmaceutical premix formulation described herein can range in part based on the volume of the flexible container containing the formulation, per bag. For example, each ready to use bag containing the formulation disclosed herein could represent approximately a day's supply of medication which is appropriate for providing hemodynamic support in septic shock associated hypotension in adult patients. For example, each 250 ml ready to use bag described herein contains about 20 mg, about 25 mg, about 40 mg, about 50 mg or about 100 mg phenylephrine HCl. In some embodiments, the pharmaceutical premix formulation provided herein comprises about 20 mg of phenylephrine HCl. In some embodiments, the pharmaceutical premix formulation provided herein comprises about 25 mg of phenylephrine HCl. In some other embodiments, the pharmaceutical premix formulation provided herein comprises about 40 mg of phenylephrine HCl. In some other embodiments, the pharmaceutical premix formulation provided herein comprises about 50 mg of phenylephrine HCl. In some other embodiments, the pharmaceutical premix formulation provided herein comprises about 100 mg of phenylephrine HCl. The dose may be a variable based on patient weight and patient response.

In one embodiment, a method of treating a human subject having a septic shock associated hypotension or anesthesia, is described herein. The method comprises the steps of obtaining the flexible container provided herein comprising the pharmaceutical premix formulation described herein, placing the flexible container on a hook or means for suspending the flexible container, and intravenously administering the pharmaceutical premix formulation of phenylephrine into the human subject.

In another embodiment, a method of treating a septic shock associated hypotension or anesthesia in a human subject in need thereof is provided. The method comprises intravenously administering to the human subject a pharmaceutical premix formulation described herein comprising from about 0.05 mg/ml to about 0.5 mg/ml, such as for example about 0.05, about 0.1, about 0.15, about 0.2, about 0.25, about 0.3, about 0.35, about 0.4, about 0.45, or about 0.5 mg/ml, more preferably from about 0.08 mg/ml to about 0.4 mg/ml, of phenylephrine HCl. In some embodiments, the pharmaceutical premix formulation in the method described above further comprises about 0.8% to about 0.9% sodium chloride. In some embodiments, the liquid formulation in the method described above further comprises about 0.08 mg sodium citrate dihydrate and about 0.02 mg citric acid monohydrate. In one embodiment, the method comprises intravenously administering a pharmaceutical premix formulation comprising about 0.08 mg/ml phenylephrine, about 0.9% sodium chloride, about 0.08 mg sodium citrate dihydrate and 0.02 mg citric acid monohydrate, to the human subject. In one embodiment, the method comprises intravenously administering a pharmaceutical premix formulation comprising about 0.1 mg/ml phenylephrine HCl, 0.9% sodium chloride, about 0.08 mg sodium citrate dihydrate and about 0.02 mg citric acid monohydrate, to the human subject. In one embodiment, the method comprises intravenously administering a pharmaceutical premix formulation comprising about 0.16 mg/ml phenylephrine HCl, about 0.9% sodium chloride, about 0.08 mg sodium citrate dihydrate and about 0.02 mg citric acid monohydrate, to the human subject. In one embodiment, the method comprises intravenously administering a pharmaceutical premix formulation comprising about 0.2 mg/ml phenylephrine HCl, about 0.9% sodium chloride, about 0.08 mg sodium citrate dihydrate and about 0.02 mg citric acid monohydrate, to the human subject. In another embodiment, the method comprises intravenously administering a pharmaceutical premix formulation comprising about 0.4 mg/ml phenylephrine HCl, about 0.9% sodium chloride, about 0.08 mg sodium citrate dihydrate and about 0.02 mg citric acid monohydrate, to the human subject.

In one embodiment, the method comprises intravenously administering a pharmaceutical premix formulation comprising about 20 mg of phenylephrine HCl at a concentration of about 0.08 mg/ml, 9.0 mg/ml sodium chloride, 0.08 mg sodium citrate dihydrate, about 0.02 mg citric acid monohydrate, and has a pH from about 3.0 to about 6.5, to the human subject. In one embodiment, the method comprises intravenously administering a pharmaceutical premix formulation comprising about 25 mg of phenylephrine HCl at a concentration of about 0.1 mg/ml, about 9.0 mg/ml sodium chloride, about 0.08 mg sodium citrate dihydrate, about 0.02 mg citric acid monohydrate, and has a pH from about 3.0 to about 6.5, to the human subject. In one embodiment, the method comprises intravenously administering a pharmaceutical premix formulation comprising about 40 mg of phenylephrine HCl at a concentration of about 0.16 mg/ml, about 9.0 mg/ml sodium chloride, about 0.08 mg sodium citrate dihydrate, about 0.02 mg citric acid monohydrate, and has a pH from about 3.0 to about 6.5, to the human subject. In one embodiment, the method comprises intravenously administering a pharmaceutical premix formulation comprising about 50 mg of phenylephrine HCl at a concentration of about 0.2 mg/ml, about 9.0 mg/ml sodium chloride, about 0.08 mg sodium citrate dihydrate, about 0.02 mg citric acid monohydrate, and has a pH from about 3.0 to about 6.5, to the human subject. In one embodiment, the method comprises intravenously administering a pharmaceutical premix formulation comprising about 100 mg of phenylephrine HCl at a concentration of about 0.4 mg/ml, about 9.0 mg/ml sodium chloride, about 0.08 mg sodium citrate dihydrate, about 0.02 mg citric acid monohydrate, and has a pH from about 3.0 to about 6.5, to the human subject.

In many embodiments of the methods described herein, phenylephrine HCl is administered as an initial dose of 40 to 100 μg by intravenous bolus to treat hypotension during anesthesia. Additional doses may be administered every 1-2 minutes as needed, not to exceed a total dosage of 200 μg. If blood pressure is below the target goal, a continuous intravenous infusion is started with an infusion rate of 10 to 35 μg/minute, not to exceed 200 μg/minute. Dosage is adjusted according to the blood pressure goal.

In certain embodiments of the methods described herein, phenylephrine HCl is administered as a continuous intravenous dose to a human subject with septic or other vasodilatory shock at an infusion rate of between about 0.5 μg/kg/min and about 6 μg/kg/min or between about 0.5 μg/kg/min and about 1.0 μg/kg/min, or between about 0.5 μg/kg/min and about 1.5 μg/kg/min, or between about 0.5

μg/kg/min and about 2.0 μg/kg/min, or between about 0.5 μg/kg/min and about 3.0 μg/kg/min, or between about 0.5 μg/kg/min and about 4.0 μg/kg/min. or between about 0.5 μg/kg/min and about 5.0 μg/kg/min. The dosage may be adjusted periodically, such as every 10-15 minutes, to achieve the desired blood pressure goal.

In many embodiments of the methods described herein, the phenylephrine HCl is administered as a continuous intravenous dose for a period of time of between about 1 and about 10 minutes, or between about 1 and about 20 minutes, or between about 1 and about 30 minutes, or between about 1 and about 2 hours, or between about 1 and about 3 hours, or between about 1 and about 4 hours, or between about 1 and about 5 hours, or between about 1 and about 6 hours, or between about 1 and about 7 hours, or between about 1 and about 8 hours, or between about 1 and about 9 hours, or between about 1 and about 10 hours, or between about 1 and about 11 hours, or between about 1 and about 12 hours, or between about 1 and about 13 hours, or between about 1 and about 14 hours, or between about 1 and about 15 hours, or between about 1 and about 16 hours, or between about 1 and about 17 hours, or between about 1 and about 18 hours, or between about 1 and about 19 hours, or between about 1 and about 20 hours, or between about 1 and about 21 hours, or between about 1 and about 22 hours, or between about 1 and about 23 hours, or between about 1 and about 24 hours.

To provide hemodynamic support in septic shock associated hypotension in adult patients, the suggested dosing infusion rate of intravenously administered phenylephrine HCl is 0.5 μg/kg/min to 6 μg/kg/min, and is titrated to achieve a desired mean arterial pressure (MAP). The dosage may be adjusted periodically, such as every 1-2 minutes, as needed, to achieve the desired blood pressure goal. If blood pressure is below the target goal, a continuous intravenous infusion is started with an infusion rate of 10 to 35 μg/minute, not to exceed 200 μg/minute In certain embodiments, the pharmaceutical premix formulation disclosed herein is administered to a human subject as a perioperative treatment. In certain embodiments, the formulation can be administered as a premedication prior to an operation.

In certain embodiments, the pharmaceutical premix formulation disclosed herein do not include any other active ingredient, or therapeutic agent, other than phenylephrine HCl.

In many embodiments of the methods described above, the pharmaceutical premix formulation comprising phenylephrine HCl is stored and infused from a flexible container such as a 100 or 250 mL VIAFLO Container Closure System, which can be used for continuous infusion depending on dosage requirement. In some embodiments, the VIAFLO Container is part of an intravenous hook system such that the intravenous hook comprises the VIAFLO Container with the pharmaceutical premix formulation of phenylephrine.

The total mg of phenylephrine HCl in the premix formulation described herein (also described in terms of the amount of premix formulation in a flexible container) can be, for example 10-120 mg. In one embodiment, a flexible container is a ready to use bag, e.g., a container closure system such as VIAFLO, and contains 20 mg of phenylephrine in 250 ml, so the flexible container comprises approximately a day's supply of medication which is appropriate for the continuous infusion protocol to treat septic shock associated with hypotension or anesthesia. In one embodiment, a flexible container is a ready to use bag. e.g., a container closure system such as VIAFLO, and contains 25 mg of phenylephrine HCl in 250 ml, so the flexible container comprises approximately a day's supply of medication which is appropriate for the continuous infusion protocol to treat septic shock associated with hypotension or anesthesia. In one embodiment, a flexible container is a ready to use bag, e.g., a container closure system such as VIAFLO, and contains 40 mg of phenylephrine HCl in 250 ml, so the flexible container comprises approximately a day's supply of medication which is appropriate for the continuous infusion protocol to treat septic shock associated with hypotension or anesthesia. In one embodiment, a flexible container is a ready to use bag, e.g., a container closure system such as VIAFLO, and contains 50 mg of phenylephrine HCl in 250 ml, so the flexible container comprises approximately a day's supply of medication which is appropriate for the continuous infusion protocol to treat septic shock associated with hypotension or anesthesia. In another embodiment, a flexible container is a ready to use bag, e.g., a container closure system such as VIAFLO, and contains 100 mg of phenylephrine HCl in 250 ml, so the flexible container comprises approximately a day's supply of medication which is appropriate for the continuous infusion protocol to treat septic shock associated with hypotension or anesthesia.

In certain embodiments, the dose of phenylephrine HCl that is administered to the human subject will be variable based on patient weight and patient response. In other embodiments, a dose of phenylephrine is administered to the subject per day, e.g., 10 to 120 mg per day. In one embodiment, 20-25 mg of phenylephrine HCl is administered to a human subject, slowly or infused over several minutes. This dose may be repeated at 10 to 15 minute intervals until adequate blood pressure is achieved. In one embodiment, 25-50 mg of phenylephrine is administered to a human subject in need thereof. e.g., a human subject experiencing mild to moderate septic shock associated hypotension or anesthesia. In another embodiment, 50-100 mg of phenylephrine HCl is administered to a human subject in need thereof, e.g., a human subject undergoing an extreme septic shock associated hypotension or anesthesia, in a 24-hour period through continuous infusion.

The formulation of phenylephrine HCl described herein may also contain a certain dose of the drug. For example, the premix formulation may contain about 20 to about 100 mg of phenylephrine HCl. A bag (or flexible container) containing the premix formulation is ready to use and does not require dilution prior to administration as the bag (or flexible container) provides the required dosage regimen (IV bolus/Infusion) to the patient based on the requirement.

In one embodiment, a flexible container, e.g., an IV bag, contains 250 mL of a premix formulation containing about 20 mg of phenylephrine HCl at a concentration of about 0.08 mg/mL, about 9.0 mg/ml sodium chloride, and has a pH from about 3.0 to about 6.5. In one embodiment, a flexible container, e.g., an IV bag, contains 250 mL of a premix formulation containing about 25 mg of phenylephrine HCl at a concentration of about 0.1 mg/mL, about 9.0 mg/ml sodium chloride, and has a pH from about 3.0 to about 6.5. In one embodiment, a flexible container, e.g., an IV bag, contains 250 mL of a premix formulation containing about 40 mg of phenylephrine HCl at a concentration of about 0.16 mg/mL, about 9.0 mg/ml sodium chloride, and has a pH from about 3.0 to about 6.5. In one embodiment, a flexible container, e.g., an IV bag, contains 250 mL of a premix formulation containing about 50 mg of phenylephrine HCl at a concentration of about 0.2 mg/mL, about 9.0 mg/ml sodium chloride, and has a pH from about 3.0 to about 6.5. In one embodiment, a flexible container, e.g., an IV bag, contains 250 mL of a premix formulation containing about 100 mg of phenylephrine HCl at a concentration of about 0.4 mg/mL, about 9.0 mg/ml sodium chloride, and has a pH from about 3.0 to about 6.5. The formulations described herein may also contain sodium hydroxide (e.g., 0.3 mg/ml) and if necessary, hydrochloric acid to adjust pH (e.g., 0.22 mg/ml HCl).

All methods described herein can be performed in any suitable order unless otherwise indicated herein or otherwise clearly contradicted by context. The use of any and all examples, or exemplary language (e.g., "such as") provided herein, is intended merely to better illustrate the materials and methods and does not pose a limitation on the scope unless otherwise claimed. No language in the specification should be construed as indicating any non-claimed element as essential to the practice of the disclosed materials and methods.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the claimed embodiments. All of the various embodiments, aspects, and options disclosed herein can be combined in all variations. The scope of the compositions, formulations, methods, and processes described herein include all actual or potential combinations of embodiments, aspects, options, examples, and preferences herein.

Although the technology herein has been described with reference to particular embodiments, it is to be understood that these embodiments are merely illustrative of the principles and applications of the present technology. It will be apparent to those skilled in the art that various modifications and variations can be made to the method and apparatus of the present technology without departing from the spirit and scope of the technology. Thus, it is intended that the present technology include modifications and variations that are within the scope of the appended claims and their equivalents.

Reference throughout this specification to "one embodiment," "certain embodiments," "one or more embodiments" or "an embodiment" means that a particular feature, structure, material, or characteristic described in connection with the embodiment is included in at least one embodiment of the technology. Thus, the appearances of phrases such as "in one or more embodiments," "in certain embodiments." "in one embodiment" or "in an embodiment" in various places throughout this specification are not necessarily referring to the same embodiment of the technology. Furthermore, the particular features, structures, materials, or characteristics may be combined in any suitable manner in one or more embodiments. Any ranges cited herein are inclusive.

Aspects of the present technology ae more fully illustrated with reference to the following examples. Before describing several exemplary embodiments of the technology, it is to be understood that the technology is not limited to the details of construction or process steps set forth in the following description. The technology is capable of other embodiments and of being practiced or being carried out in various ways. The following examples are set forth to illustrate certain aspects of the present technology and are not to be construed as limiting thereof.

EXAMPLES

The following examples support the concept of an aqueous, pharmaceutical premix phenylephrine formulation which is ready to use and does not require dilution. Further, the premix phenylephrine formulations are stable, including at room temperature. The examples support a product for treating hypotension in a human patient requiring phenylephrine HCl via intravenous infusion. The following examples are included for illustrative purposes only and are not intended to limit the scope of the invention.

Example 1: Long Term Stability of Phenylephrine Premix Formulations

The following example provides stability data for premix phenylephrine formulations having concentrations of phenylephrine HCl ranging from 0.08 mg/mL to 0.4 mg/mL, sodium citrate dihydrate and citric acid monohydrate (buffer), in 0.9% sodium chloride, and having a pH ranging from 3.0 to 6.5 (with sodium hydroxide and hydrochloric acid used as pH adjustors).

The following formulations were used in experiments in this example:

- phenylephrine HCl at 0.08 ml/ml or 0.4 mg/ml. pH 3.0.0.9% NaCl;
- phenylephrine HCl at 0.08 ml/ml or 0.4 mg/ml, pH 3.5, 0.9% NaCl;
- phenylephrine HCl at 0.08 ml/ml or 0.4 mg/ml, pH 5.5, 0.9% NaCl;
- phenylephrine HCl at 0.08 ml/ml or 0.4 mg/ml, pH 6.5, 0.9% NaCl.

The above formulations also contained sodium citrate dihydrate and citric acid monohydrate. Various conditions were tested, and degradants (phenylephrone and phenylephrine-citrate) were determined. These degradants are reflective of the stability of the formulation.

TABLE 1 pH stability data for a premix formulation with 0.08 mg/ml phenylephrine HCl at pH 3.0

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 3.08 | ND | ND | ND | ND | 101.4 |
| 1 M-40° C. ± 2° C./ NMT 25% RH | * | ** | <A | 3.06 | ND | ND | 0.043 | 0.079 | 100.4 |
| 3 M-40° C. ± 2° C./ NMT 25% RH | * | ** | <A | 3.06 | ND | ND | 0.043 | 0.043 | 101.0 |

TABLE 1-continued pH stability data for a premix formulation with 0.08 mg/ml phenylephrine HCl at pH 3.0

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| 6 M-40° C. ± 2° C./ NMT 25% RH | * | ** | <A | 2.99 | 0.001 | ND | 0.047 (RRT-4.11) 0.021 (RRT-0.79) | 0.079 | 100.8 |
| 3 M- 25° C ± 2° C/ 40% ± 5 % RH | * | ** | <A | 3.03 | ND | ND | 0.039 | 0.039 | 100.8 |
| 6 M-25° C ± 2° C/ 40% ± 5% RH | * | ** | <A | 2.93 | ND | ND | 0.015 (RRT-0.79) 0.014 (RRT-4.12) | 0.029 | 100.6 |
| 12 M 25° C. ± 2° C./ 40% ± 5% RH | * | ** | <A | 3.04 | 0.003 | ND | 0.025 (RRT-3.76) | 0.114 | 101.9 |

* Clear, colorless solution

** Clear solution essentially free from visible particulate matter

<A: Color of solution is less intense than the USP matching fluid A

ND: Not detected

For above table (and tables throughout), the time period-temperature of testing/humidity conditions are presented. For example, "6M-40° C. ± 2° C./ NMT 25% RH" indicates a 6 month period of testing at 40 degrees Celsius ± 2 degrees Celsius at not more than (NMT) 25% relative humidity (RH).

TABLE 2 pH stability data for a premix formulation with 0.08 mg/ml phenylephrine HCl at pH 3.5

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 3.59 | ND | ND | 0.037 (RRT-3.65) | 0.065 | 100.3 |
| 1 M-40° C. ± 2° C./ NMT 25% RH | * | ** | <A | 3.61 | ND | ND | 0.039 (RRT-3.61) | 0.069 | 101.1 |
| 3 M-40° C. ± 2° C./ NMT 25% RH | * | ** | <A | 3.61 | ND | ND | ND | ND | 101.2 |
| 6 M-40° C. ± 2° C./ NMT 25% RH | * | ** | <A | 3.49 | ND | ND | 0.027 (RRT-0.79) 0.017 (RRT-1.2) | 0.044 | 102.0 |
| 3 M-25° C ± 2° C./ 40% ± 5% RH | * | ** | <A | 3.59 | ND | ND | ND | ND | 100.9 |
| 6 M-25° C. ± 2° C./ 40% ± 5% RH | * | ** | <A | 3.51 | ND | ND | 0.026 (RRT-0.79) 0.011 (RRT-0.54) | 0.037 | 101.0 |
| 12 M 25° C. ± 2° C./ 40% ± 5% RH | * | ** | <A | 3.63 | 0.002 | ND | 0.032 (RRT-0.77) 0.020 (RRT-1.19) | 0.099 | 101.8 |

* Clear, colorless solution

\# Clear solution essentially free from visible particulate matter

@ Color of solution is less intense than the USP matching fluid A

ND: Not detected

TABLE 3 pH stability data for a premix formulation with 0.08 mg/ml phenylephrine HCl at pH 5.5

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 5.60 | ND | ND | 0.042 (RRT-3.65) | 0.061 | 100.0 |
| 1 M-40° C. ± 2° C./ NMT 25% RH | * | ** | <A | 5.65 | ND | ND | 0.091 (RRT-3.66) | 0.115 | 100.9 |
| 3 M-40° C. ± 2° C./ NMT 25% RH | * | ** | <A | 5.57 | ND | ND | 0.069 (RRT-3.66) | 0.069 | 100.8 |
| 6 M-40° C. ± 2° C./ NMT 25% RH | * | ** | <A | 5.14 | 0.005 | ND | 0.063 (RRT-3.8) 0.036 (RRT-2.57) 0.045 (RRT-3.96) | 0.213 | 101.3 |
| 3 M-25° C. ± 2° C./ 40% ± 5% RH | * | ** | <A | 5.63 | ND | ND | 0.072 (RRT-3.66) | 0.072 | 100.4 |
| 6 M-25° C ± 2° C./ 40% ± 5% RH | * | ** | <A | 5.61 | ND | ND | 0.058 (RRT-3.8) 0.022 (RRT-0.79) 0.014 (RRT-0.54) | 0.094 | 100.5 |
| 12 M 25° C. ± 2° C./ 40% ± 5% RH | * | ** | <A | 5.63 | 0.006 | ND | 0.030 (RRT-1.19) 0.027 (RRT-0.77) | 0.125 | 100.7 |

* A clear and colorless solution filled in a bag
** Clear solution essentially free from visible particulate matter.
<A: Color of the solution is less intense than USP matching fluid A.
ND = Not detectable

TABLE 4 pH stability data for a premix formulation with 0.08 mg/ml phenylephrine HCl at pH 6.5

| Condition (Time point Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 6.43 | ND | ND | 0.1 | 0.150 | 99.9 |
| 1 M-40° C. ± 2° C./ NMT 25% RH | * | ** | <A | 6.39 | ND | ND | 0.043 | 0.043 | 100.7 |

* A clear and colorless solution filled in a bag
** Clear solution essentially free from visible particulate matter.
<A: Color of the solution is less intense than USP matching fluid A.
ND = Not detectable

TABLE 5 pH stability data for a premix formulation with 0.4 mg/ml phenylephrine HCl at pH 3.0

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 3.08 | ND | ND | 0.012 (RRT2.91) | 0.012 | 100.8 |
| 1 M-40° C. ± 2° C./ NMT 25% RH | * | ** | <A | 3.06 | ND | ND | 0.013 (RRT-0.78) | 0.013 | 100.2 |
| 3 M-40° C. ± 2° C./ NMT 25% RH | * | ** | <A | 3.01 | ND | ND | ND | ND | 100.1 |
| 6 M-40° C. ± 2° C./ NMT 25% RH | * | ** | <A | 3.01 | ND | ND | 0.017 (RRT-0.8) 0.007 (RRT-1.2) | 0.024 | 101.1 |
| 3 M-25° C. ± 2° C./ 40% ± 5% RH | * | ** | <A | 2.98 | ND | ND | ND | ND | 100.1 |
| 6 M-25° C. ± 2° C./ 40% ± 5% RH | * | ** | <A | 3.00 | ND | ND | 0.015 (RRT-0.079) | 0.015 | 100.1 |
| 12 M-25° C. ± 2° C./ 40% ± 5% RH | * | ** | <A | 3.04 | 0.0 | ND | 0.016 (RRT-2.63) | 0.038 | 101.06 |

* A clear and colorless solution filled in a bag
** Clear solution essentially free from visible particulate matter.
<A: Color of the solution is less intense than USP matching fluid A
ND: Not detected

TABLE 6 pH stability data for a premix formulation with 0.4 mg/ml phenylephrine HCl at pH 3.5.

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 3.58 | ND | ND | 0.053 (RRT-0.78) | 0.053 | 100.1 |
| 1 M-40° C. ± 2° C./ NMT 25% RH | * | ** | <A | 3.80 | ND | ND | ND | ND | 100.2 |
| 3 M-40° C. ± 2° C./ NMT 25% RH | * | ** | <A | 3.52 | ND | ND | 0.025 (RRT-3.54) | 0.103 | 99.5 |
| 6 M-40° C. ± 2° C./ NMT 25% RH | * | ** | <A | 3.46 | ND | ND | ND | ND | 102.9 |
| 3 M-25° C. ± 2° C./ 40% ± 5% RH | * | ** | <A | 3.51 | ND | ND | ND | 0.084 | 99.8 |
| 6 M-25° C. ± 2° C./ 40% ± 5% RH | * | ** | <A | 3.51 | ND | ND | ND | ND | 102.3 |
| 12 M 25° C. ± 2° C./ 40% ± 5% RH | * | ** | <A | 3.67 | ND | ND | 0.013 (RRT-1.19) | 0.023 | 100.84 |

* A clear and colorless solution filled in a bag
** Clear solution essentially free from visible particulate matter.
<A: Color of the solution is less intense than USP matching fluid A.
ND: Not detected

TABLE 7 pH stability data for a premix formulation with 0.4 mg/ml phenylephrine HCl at pH 5.5

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 5.60 | ND | ND | 0.049 (RRT-4.23) | 0.097 | 100.0 |
| 1 M-40° C. ± 2° C./ NMT 25% RH | * | ** | <A | 5.60 | ND | ND | 0.037 (RRT-3.24) | 0.086 | 100.14 |
| 3 M-40° C. ± 2° C./ NMT 25% RH | * | ** | <A | 5.45 | ND | ND | 0.05 (RRT-1.5)<br>0.022 (RRT-3.54) | 0.122 | 99.4 |
| 6 M-40° C. ± 2° C./ NMT 25% RH | * | ** | <A | 5.03 | ND | ND | ND | ND | 101.1 |
| 3 M-25° C. ± 2° C./ 40% ± 5% RH | * | ** | <A | 5.54 | ND | ND | 0.018 (RRT-3.54) | 0.070 | 99.0 |
| 6 M-25° C. ± 2° C./ 40% ± 5% RH | * | ** | <A | 5.17 | ND | ND | ND | ND | 100.8 |
| 12 M 25° C. ± 2° C./ 40% ± 5% RH | * | ** | <A | 5.53 | 0.004 | ND | 0.017 (RRT-1.19) | 0.032 | 101.1 |

* A clear and colorless solution filled in a bag
** Clear solution essentially free from visible particulate matter.
<A: Color of the solution is less intense than USP matching fluid A.
ND: Not detected

TABLE 8 pH stability data for a premix formulation with 0.4 me/mi phenylephrine HCl at pH 6.5

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | *** | A | 6.58 | ND | ND | 0.012 (RRT-0.78) | 0.012 | 100.9 |
| 1 M-40° C. ± 2° C./ NMT 25% RH | * | ** | <A | 6.43 | ND | ND | 0.032 (RRT-2.75) | 0.049 | 100.23 |
| 3 M-40° ± 2° C./ NMT 25% RH | * | ** | <A | 6.36 | ND | ND | 0.052 (RRT-3.55)<br>0.050 (RRT-1.5) | 0.149 | 99.7 |
| 6 M-40° ± 2° C./ NMT 25% RH | * | ** | <A | 6.43 | ND | ND | 0.063 (RRT-3.8)<br>0.060 (RRT-3.97)<br>0.028 (RRT-2.57) | 0.151 | 101.2 |
| 3 M-25° C ± 2° C./ 40% ± 5% RH | * | ** | <A | 6.41 | ND | ND | 0.028 (RRT-3.46) | 0.028 | 99.2 |
| 6 M-25° C. ± 2° C./ 40% ± 5% RH | * | ** | <A | 6.08 | ND | ND | 0.039 (RRT-3.97)<br>0.035 (RRT-3.8) | 0.074 | 101.9 |
| 12 M 25° C. ± 2° C./ 40% ± 5% RH | * | ** | <A | 6.03 | 0.005 | ND | 0.021 (RRT-1.19) | 0.065 | 101.2 |

* A clear and colorless solution filled in a bag
** Clear solution essentially free from visible particulate matter.
<A: Color of the solution is less intense than USP matching fluid A.
ND: Not detected Based on the results provided below in Tables 1-8, premix phenylephrine formulations in 0.9% sodium chloride at both 0.08 mg/ml and 0.4 ml/ml were stable in the pH range of 3.0 to 6.5 (buffered with sodium citrate dihydrate and citric acid monohydrate). This stability was tested over the course of 6 months.

Example 2: Impact of Sodium Metabisulfite (SMBS) on Premix Phenylephrine Formulations The following example describes the impact of sodium meta bisulfite (SMBS) and oxygen scavengers on premix phenylephrine formulations.

Three different approaches were taken to determine the impact of SMBS on premix formulation stability. The following premix phenylephrine formulations were tested for stability:

premix formulations containing 0.08 mg/mL, 0.1 mg/mL, 0.16 mg/mL, 0.2 mg/mL, or 0.4 mg/mL of phenylephrine HCl and 0.9% sodium chloride without SMBS and with an oxygen scavenger (Tables 9-13);

premix formulations containing 0.08 mg/mL, 0.2 mg/ml, or 0.4 mg/mL of phenylephrine HCl in 0.9% sodium chloride with SMBS and without an oxygen scavenger (Tables 14-16); and premix formulations containing 0.08 mg/ml, 0.1 mg/ml, 0.16 mg/mL, 0.4 mg/ml of phenylephrine HCl in 0.9% sodium chloride without SMBS and without an oxygen scavenger (results in Tables 17-20).

Phenylephrine premix is oxygen sensitive. Based on the data presented below, the data shows that the finished product is stable in the presence of an oxygen scavenger. SMBS acts as an antioxidant in the formulation. The data in Tables 9-13 (without SMBS and with an oxygen scavenger) indicates that formulations were relatively more stable than the formulations tested in Tables 14-20. Thus, adding SMBS did not give additional benefit in terms of finished product stability.

TABLE 9

Stability data for a premix formulation with 0.08 mg/ml phenylephrine HCl without SMBS and with oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 4.44 | ND | ND | ND | ND | 101.56 |
| 1 M-40° C. ± 2° C./ NMT 25% RH | * | ** | <A | 4.58 | 0.002 | ND | 0.005 (RRT-1.22) | 0.007 | 101.28 |
| 2 M-40° C. ± 2° C./ NMT 25% RH | * | ** | <A | 4.60 | ND | ND | 0.046 (RRT-3.64) | 0.097 | 100.3 |
| 3 M-40° C. ± 2° C./ NMT 25% RH | * | ** | <A | 4.57 | ND | ND | 0.044 (RRT-3.65) | 0.072 | 100.4 |
| 6 M-40° C. ± 2° C./ NMT 25% RH | * | ** | <A | 4.53 | ND | ND | 0.027 (RRT-2.86) 0.021 (RRT-2.51) | 0.048 | 100.8 |
| 1 M-25° C. ± 2° C./ 40% ± 5% RH | * | ** | <A | 4.58 | ND | ND | ND | ND | 101.27 |
| 2 M-25° C. ± 2° C./ 40% ± 5% RH | * | ** | <A | 4.57 | ND | ND | 0.045 | 0.068 | 100.5 |
| 3 M-25° C. ± 2° C./ 40% ± 5% RH | * | ** | <A | 4.57 | ND | ND | 0.043 | 0.069 | 100.2 |
| 6 M-25° C. ± 2° C./ 40% ± 5% RH | * | ** | <A | 4.52 | ND | ND | ND | ND | 100.5 |
| 12 M 25° C. ± 2° C./ 40% ± 5% RH | * | ** | <A | 4.64 | ND | ND | 0.032 (RRT-0.79) | 0.057 | 100.8 |

* A clear and colorless solution filled in a bag

** Clear solution essentially free from visible particulate matter.

<A: Color of the solution is less intense than USP matching fluid A.

ND: Not detected

TABLE 10

Stability data for a premix formulation with 0.1 mg/ml phenylephrine HCl without SMBS and with oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 4.53 | 0.002 | ND | 0.024 (RRT-0.52) | 0.038 | 101.1 |
| 1 M-40° C. ± 2° C./ NMT 25% RH | * | ** | <A | 4.65 | 0.002 | ND | 0.023 (RRT-0.52) | 0.054 | 101.2 |
| 2 M-40° C. ± 2° C./ NMT 25% RH | * | ** | <A | 4.65 | ND | ND | 0.036 (RRT-4.44) | 0.086 | 100.4 |
| 3 M-40° C. ± 2° C./ NMT 25% RH | * | ** | <A | 4.66 | ND | ND | 0.114 (RRT-1.23) | 0.23 | 100.2 |
| 6 M-40° C. ± 2° C./ NMT 25% RH | * | ** | <A | 4.64 | 0.008 | ND | 0.024 (RRT-1.21) | 0.135 | 102.3 |
| 1 M-25° C. ± 2° C./ 40% ± 5% RH | * | ** | <A | 4.62 | 0.002 | ND | 0.029 (RRT-0.52) | 0.051 | 100.6 |
| 2 M-25° C. ± 2° C./ 40% ± 5% RH | * | ** | <A | 4.65 | ND | ND | 0.044 (RRT-0.78) | 0.044 | 100.4 |
| 3 M-25° C. ± 2° C./ 40% ± 5% RH | * | ** | <A | 4.64 | ND | ND | 0.081 (RRT-1.23) | 0.153 | 101.1 |
| 6 M-25° C. ± 2° C./ 40% ± 5% RH | * | ** | <A | 4.64 | ND | ND | 0.046 | 0.066 | 101.9 |
| 12 M 25° C. ± 2° C./ 40% ± 5% RH | * | ** | <A | 4.69 | 0.003 | ND | 0.024 (RRT-0.77) | 0.103 | 102.6 |

* A clear and colorless solution filled in a bag

** Clear solution essentially free from visible particulate matter.

<A: Color of the solution is less intense than USP matching fluid A.

ND: Not detected

TABLE 11

Stability data for a premix formulation with 0.16 mg/ml phenylephrine HCl without SMBS with Oxygen Scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 4.53 | ND | 0.015 | 0.004 (RRT-2.37) | 0.021 | 102.28 |
| 1 M-40° C. ± 2° C./ NMT 25% RH | * | ** | <A | 4.64 | 0.001 | 0.015 | 0.005 (RRT-2.37) | 0.025 | 101.9 |
| 2 M-40° C. 2° C./ NMT 25% RH | * | ** | <A | 4.63 | ND | ND | 0.034 (RRT-0.78) | 0.034 | 100.1 |
| 3 M-40° C. ± 2° C./ NMT 25% RH | * | ** | <A | 4.67 | ND | ND | 0.035 (RRT-2.75) | 0.063 | 100.2 |
| 6 M-40° C. ± 2° C./ NMT 25% RH | * | ** | <A | 4.69 | 0.007 | ND | 0.025 (RRT-1.21) | 0.072 | 102.3 |
| 1 M-25° C. ± 2° C./ 40% ± 5% RH | * | ** | <A | 4.64 | ND | 0.014 | 0.022 (RRT-2.37) | 0.036 | 101.89 |
| 2 M-25° C. ± 2° C./ 40% ± 5% RH | * | ** | <A | 4.64 | ND | ND | 0.099 (RRT-0.78) | 0.127 | 100.0 |
| 3 M-25° C. ± 2° C./ 40% ± 5% RH | * | ** | <A | 4.63 | ND | ND | 0.021 (RRT-0.78) | 0.021 | 99.9 |
| 6 M-25° C. ± 2° C./ 40% ± 5% RH | * | ** | <A | 4.69 | ND | ND | 0.027 (RRT-0.79) | 0.027 | 101.7 |

TABLE 11-continued

Stability data for a premix formulation with 0.16 mg/ml phenylephrine HCl without SMBS with Oxygen Scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| 12 M-25° C. ± 2° C./ 40% ± 5% RH | * | ** | <A | 4.63 | 0.003 | ND | 0.015 (RRT-0.52) | 0.051 | 101.8 |

* A clear and colorless solution filled in a bag
** Clear solution essentially free from visible particulate matter.
<A: Color of the solution is less intense than USP matching fluid A.
ND: Not detected

TABLE 12

Stability data for a premix formulation with 0.2 mg/ml phenylephrine HCl without SMBS with Oxygen Scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 4.36 | ND | 0.013 | 0.003 (RRT-2.38) | 0.016 | 101.46 |
| 1 M-40° C. ± 2° C./ NMT 25% RH | * | ** | <A | 4.62 | 0.02 | ND | 0.007 (RRT-2.37) | 0.026 | 102.2 |
| 2 M-40° C. ± 2° C./ NMT 25% RH | * | ** | <A | 4.64 | ND | ND | 0.016 (RRT-0.78) | 0.016 | 100.6 |
| 3 M-40° C. 2° C./ NMT 25% RH | * | ** | <A | 4.65 | ND | ND | 0.034 (RRT-2.74) | 0.057 | 100.5 |
| 6 M-40° C. ± 2° C./ NMT 25% RH | * | ** | <A | 4.66 | 0.007 | ND | 0.023 (RRT-1.21) | 0.106 | 102.8 |
| 1 M-25° C ± 2° C./ 40% ± 5% RH | * | ** | <A | 4.64 | ND | ND | 0.007 (RRT-2.90) | 0.016 | 101.6 |
| 2 M-25° C. ± 2° C./ 40% ± 5% RH | * | ** | <A | 4.60 | ND | ND | 0.017 (RRT-0.78) | 0.017 | 100.8 |
| 3 M-25° C. ± 2° C./ 40% ± 5% RH | * | ** | <A | 4.62 | ND | ND | 0.033 (RRT-2.75) | 0.054 | 101.1 |
| 6 M-25° C. ± 2° C./ 40% ± 5% RH | * | ** | <A | 4.62 | ND | ND | 0.029 (RRT-0.79) | 0.047 | 102.0 |
| 12 M-25° C. ± 2° C./ 40% ± 5% RH | * | ** | <A | 4.67 | 0.003 | ND | 0.014 (RRT-4.15) | 0.057 | 103.5 |

* A clear and colorless solution filled in a bag
** Clear solution essentially free from visible particulate matter.
<A: Color of the solution is less intense than USP matching fluid A.
ND: Not detected

TABLE 13

Stability data for a premix formulation with 0.4 mg/ml phenylephrine HCl without SMBS with oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 4.55 | 0.001 | ND | 0.006 (RRT-2.7) | 0.011 | 101.37 |
| 1 M - 40° C. ± 2° C./ NMT 25% RH | * | ** | <A | 4.66 | 0.001 | ND | 0.011 (RRT-2.4) | 0.026 | 102.1 |
| 2 M - 40° C. ± 2° C./ NMT 25% RH | * | ** | <A | 4.67 | ND | ND | 0.009 (RRT-0.78) | 0.015 | 100.1 |
| 3 M - 40° C. ± 2° C./ NMT 25% RH | * | ** | <A | 4.69 | ND | ND | 0.055 (RRT-0.78) | 0.055 | 100.8 |
| 6 M- 40° C. ± 2° C./ NMT 25% RH | * | ** | <A | 4.63 | ND | ND | 0.058 (RRT-0.78) | 0.087 | 100.2 |
| 1 M- 25° C. ± 2° C./ 40% ± 5% RH | * | ** | <A | 4.66 | ND | ND | 0.005 (RRT-2.7) | 0.008 | 101.9 |
| 2 M- 25° C. ± 2° C./ 40% ± 5% RH | * | ** | <A | 4.57 | ND | ND | 0.011 (RRT-0.78) | 0.011 | 100.5 |
| 3 M- 25° C. ± 2° C./ 40% ± 5% RH | * | ** | <A | 4.64 | ND | ND | 0.057 (RRT-0.78) | 0.057 | 100.4 |
| 6 M- 25° C. ± 2° C./ 40% ± 5% RH | * | ** | <A | 4.60 | ND | ND | 0.055 (RRT-0.78) | 0.055 | 99.7 |
| 12 M - 25° C. ± 2° C./ 40% ± 5% RH | * | ** | <A | 4.7 | ND | ND | 0.060 (RRT-0.95) | 0.071 | 100.82 |

* A clear and colorless solution filled in a bag

** Clear solution essentially free from visible particulate matter.

<A: Color of the solution is less intense than USP matching fluid A.

ND: Not detected

TABLE 14

Stability data for a premix formulation with 0.08 mg/ml phenylephrine HCl with SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| Initial | * | ** | <A | 3.63 | 0.232 | ND | 0.114 (RRT-0.46) 0.080 (RRT-0.50) 0.064 (RRT-0.54) | 0.538 | 100.58 | 28.73 |
| 1 M - 40° C. ± 2° C./ NMT 25% RH | * | ** | <A | 3.48 | 0.326 | ND | 0.143 (RRT-0.41) 0.116 (RRT-0.45) 0.103 (RRT-0.52) | 0.717 | 99.29 | ND |

TABLE 14-continued

Stability data for a premix formulation with 0.08 mg/ml phenylephrine HCl with SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenyl-ephrine HCl Between 90.0% and 115.0% of the label claim of Phenylephrine Hydrochloride | Assay of Sodium Meta-bisulfite |
|---|---|---|---|---|---|---|---|---|---|---|
| 2 M - 40° C. ± 2° C./ NMT 25% RH | * | ** | <A | 3.48 | 0.304 | ND | 0.163 (RRT-0.42) 0.124 (RRT-3.28) 0.113 (RRT-0.47) 0.071 (RRT-0.51) 0.067 (RRT-2.22) | 0.842 | 100.59 | ND |
| 3 M- 40° C. ± 2°C/ NMT 25% RH | * | ** | <A | 3.51 | 0.343 | ND | 0.169 (RRT-0.46) 0.090 (RRT-0.53) 0.088 (RRT-0.51) 0.065 (RRT-2.48) | 0.755 | 100.50 | ND |
| 6 M- 40° C. ± 2° C./ NMT 25% RH | * | ** | <A | 3.51 | 0.269 | 0.026 | 0.148 (RRT-3.33) 0.077 (RRT-0.43) 0.053 (RRT-0.47) 0.081 (RRT-0.52) | 0.861 | 101.05 | ND |
| 1 M- 25° C. ± 2° C./ 40% ± 5% RH | * | ** | <A | 3.55 | 0.294 | ND | 0.105 (RRT-0.45) 0.098 (RRT-0.41) 0.087 (RRT-0.52) | 0.601 | 99.45 | 19.8 |
| 2 M- 25° C. ± 2° C./ 40% ± 5% RH | * | ** | <A | 3.56 | 0.209 | ND | 0.128 (RRT-0.42) 0.125 (RRT-3.27) 0.102 (RRT-0.47) 0.059 (RRT-2.22) | 0.623 | 100.82 | 14.44 |
| 3 M- 25° C. ± 2° C./ 40% ± 5% RH | * | ** | <A | 3.69 | 0.245 | ND | 0.136 (RRT-0.46) 0.070 (RRT-2.48) | 0.451 | 100.59 | 15.94 |
| 6 M- 25° C. ± 2° C./ 40% ± 5% RH | * | ** | <A | 3.67 | 0.253 | ND | 0.111 (RRT-0.47) 0.107 (RRT-0.43) 0.089 (RRT-2.24) | 0.669 | 101.31 | ND |
| 12 M - 25° C. ± 2° C./ 40% ± 5% RH | * | ** | <A | 3.53 | 0.139 | ND | 0.073 (RRT-0.48) 0.071 (RRT-3.77) 0.042 (RRT-0.52) 0.043 (RRT-3.85) | 0.504 | 100.2 | 3.34 |

* Clear, colorless solution

\# Clear solution essentially free from visible particulate matter

@ Color of solution is less intense than the USP matching fluid A

ND: Not detected

TABLE 15

Stability data for a premix formulation with 0.4 mg/ml phenylephrine HCl, terminal sterilization, with SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| Initial | * | ** | <A | 4.38 | 0.149 | ND | 0.067 (RRT-0.45) 0.086 (RRT-0.41) 0.042 (RRT-0.50) | 0.344 | 100.57 | 42.66 |
| 1 M - 40° C. ± 2° C./NMT 25% RH | * | ** | <A | 3.74 | 0.203 | ND | 0.076 (RRT-2.49) 0.066 (RRT-0.46) 0.063 (RRT-0.51) | 0.408 | 100.34 | 22.36 |
| 2 M - 40° C. ± 2° C./NMT 25% RH | * | ** | <A | 3.50 | 0.281 | ND | 0.139 (RRT-0.43) 0.127 (RRT-0.48) 0.105 (RRT-0152) 0.091 (RRT-2.25) | 0.849 | 100.15 | 1.07 |
| 3 M- 40° C. ± 2° C./NMT 25% RH | * | ** | <A | 3.55 | 0.265 | ND | 0.129 (RRT-0.43) 0.120 (RRT-0.48) 0.0879 RRT-0.52) | 0.786 | 100.19 | 8.98 |
| 1 M- 25° C. ± 2° C./40% ± 5% RH | * | ** | <A | 3.85 | 0.156 | ND | ND | 0.156 | 100.41 | 46.86 |
| 2 M-25° C. ± 2° C./40% ± 5% RH | * | ** | <A | 3.65 | 0.222 | ND | 0.098 (RRT-0.43) 0.068 (RRT-0.48) 0.066 (RRT-0.52) 0.069 (RRT-2.25) | 0.543 | 99.68 | 30.47 |
| 3 M-25° C. ± 2° C./40% ± 5% RH | * | ** | <A | 3.70 | 0.210 | ND | 0.092 (RRT-0.43) 0.092 (RRT-0.48) 0.064 (RRT-2.25) | 0.531 | 100.34 | 24.78 |
| 9 M - 25° C. ± 2° C./40% ± 5% RH | * | ** | <A | 3.61 | 0.120 | ND | 0.063 (RRT-0.48) 0.043 (RRT-0.52) 0.035 (RRT-2.51) | 0.305 | 100.04 | 15.23 |
| 12 M- 25° C. ± 2° C./40% ± 5% RH | * | ** | <A | 3.72 | 0.246 | ND | 0.098 (RRT-0.51) 0.050 (RRT-0.53) 0.061 (RRT-0.79) 0.042 (RRT-3.98) | 0.523 | 101.05 | 17.48 |

* A clear and colorless solution filled in a bag

** Clear solution essentially free from visible particulate matter.

<A: Color of the solution is less intense than USP matching fluid A.

ND: Not detected

TABLE 16

Stability data for a premix formulation with 0.2 mg/ml phenylephrine, terminal sterilization, with SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| Initial | * | ** | <A | 3.58 | 0.395 | ND | 0.144 (RRT-0.48) 0.137 (RRT-0.44) 0.081 (RRT-0.53) 0.039 (RRT-0.73) | 0.796 | 99.38 | 24.34 |
| 1 M - 40° C. ± 2° C./ NMT 25% RH | * | ** | <A | 3.48 | 0.379 | ND | 0.176 (RRT-0.41) 0.174 (RRT-0.45) 0.105 (RRT-0.52) | 0.834 | 99.04 | 7.27 |
| 2 M - 40° C. ± 2° C./ NMT 25% RH | * | ** | <A | 3.53 | 0.321 | ND | 0.201 (RRT-0.40) 0.160 (RRT-0.45) 0.149 (RRT-2.13) 0.119 (RRT-0.50) | 0.950 | 99.47 | 4.53 |
| 3 M- 40° C. ± 2° C./ NMT 25% RH | * | ** | <A | 3.42 | 0.406 | ND | 0.251 (RRT-0.46) 0.182 (RRT-2.49) 0.137 (RRT-0.51) 0.100 (RRT-0.80) 0.097 (RRT-0.53) | 1.173 | 100.47 | ND |
| 6 M- 40° C. ± 2° C./ NMT 25% RH | * | ** | <A | 3.49 | 0.365 | 0.012 | 0.166 (RRT-0.43) 0.112 (RRT-0.47) 0.142 (RRT-0.52) 0.126 (RRT-2.22) | 1.035 | 100.96 | 0.97 |
| 3 M- 25° C. ± 2° C./ 40% ± 5% RH | * | ** | <A | 3.64 | 0.283 | ND | 0.127 (RRT-0.46) 0.118 (RRT-2.49) 0.092 (RRT-0.51) | 0.620 | 101.03 | 31.70 |
| 6 M- 25° C. ± 2° C./ 40% ± 5% RH | * | ** | <A | 3.70 | 0.316 | ND | 0.149 (RRT-0.47) 0.133 (RRT-0.43) 0.127 (RRT-2.22) 0.073 (RRT-0.52) | 0.853 | 100.63 | 26.43 |

* A clear and colorless solution filled in a bag

** Clear solution essentially free from visible particulate matter.

<A: Color of the solution is less intense than USP matching fluid A.

ND: Not detected

Phenylephrine HCl premix formulations in Tables 14-16 contained the SMBS in the formulation without an oxygen scavenger. The stability data revealed that the formulation is relatively less stable in the absence of oxygen scavenger & presence of SMBS in the formulation.

TABLE 17

Stability data for a premix formulation with 0.08 mg/ml phenylephrine HCl without SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenyl-ephrone (phenyl-ephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial (Autoclaved) | * | ** | <A | 4.37 | ND | ND | ND | ND | 100.8 |
| 1 M - 40° C. ± 2° C./NMT 25% RH | * | ** | <A | 4.43 | ND | ND | 0.049 (RRT-0.51) | 0.049 | 99.8 |
| 2 M - 40° C. ± 2° C./NMT 25% RH | * | ** | <A | 4.39 | ND | ND | 0.086 (RRT-0.52) | 0.086 | 100.7 |
| 3 M - 40° C. ± 2° C./NMT 25% RH | * | ** | <A | 4.46 | ND | ND | 0.186 (RRT-0.53) | 0.186 | 100.5 |
| 6 M - 40° C. ± 2° C./NMT 25% RH | * | ** | <A | 4.61 | 0.019 | 0.03 | 0.299 (RRT-0.52), 0.288 (RRT-4.06) | 0.937 | 99.3 |
| 1 M - 25° C. ± 2° C./40% ± 5% RH | * | ** | <A | 4.59 | ND | ND | ND | ND | 99.8 |
| 2 M - 25° C. ± 2° C./40% ± 5% RH | * | ** | <A | 4.55 | ND | ND | ND | ND | 101.1 |
| 3 M - 25° C. ± 2° C./40% ± 5% RH | * | ** | <A | 4.56 | ND | ND | ND | ND | 100.8 |
| 6 M - 25° C. ± 2° C./40% ± 5% RH | * | ** | <A | 4.67 | 0.013 | ND | 0.048 (RRT-0.52), 0.034 (RRT-4.06) | 0.139 | 101.1 |
| 9 M - 25° C. ± 2° C./40% ± 5% RH | * | ** | <A | 4.50 | ND | ND | 0.067 (RRT-4.39) 0.035 (RRT-3.66) 0.099 (RRT-0.78) | 0.201 | 100.6 |
| 12 M - 25° C. ± 2° C./40% ± 5% RH | * | ** | <A | 4.62 | 0.002 | ND | 0.037 (RRT-0.79) 0.037 (RRT-0.54) 0.010 (RRT-1.2) | 0.086 | 100.5 |

* A clear and colorless solution filled in a bag

** Clear solution essentially free from visible particulate matter.

<A: Color of the solution is less intense than USP matching fluid A.

ND: Not detected

TABLE 18

Stability data for a premix formulation with 0.1 mg/ml phenylephrine HCl without SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial | * | ** | <A | 4.54 | ND | ND | ND | ND | 98.90 |
| 1 M - 40° C. ± 2° C./NMT 25% RH | * | ** | <A | 4.53 | ND | ND | ND | ND | 100.72 |
| 2 M - 40° C. ± 2° C./NMT 25% RH | * | ** | <A | 4.49 | 0.005 | 0.025 | 0.077 (RRT-0.52) 0.064 (RRT-4.06) | 0.275 | 101.04 |
| 3 M - 40° C. ± 2° C./NMT 25% RH | * | ** | <A | 4.53 | 0.006 | 0.027 | 0.108 (RRT-0.52) 0.048 (RRT-4.03) | 0.282 | 100.96 |
| 6 M - 40° C. ± 2° C./NMT 25% RH | * | ** | <A | 4.55 | ND | ND | 0.285 (RRT-4.41) 0.130 (RRT-3.35) 0.080 (RRT-4.67) | 1.197 | 97.2 |
| 1 M - 25° C. ± 2° C./40% ± 5% RH | * | ** | <A | 4.54 | ND | ND | ND | ND | 100.50 |
| 2 M - 25° C. ± 2° C./40% ± 5% RH | * | ** | <A | 4.52 | 0.003 | ND | 0.025 (RRT-0.52) 0.025 (RRT-3.37) | 0.109 | 101.12 |
| 3 M - 25° C. ± 2° C./40% ± 5% RH | * | ** | <A | 4.54 | 0.003 | ND | 0.022 (RRT-0.52) 0.030 (RRT-4.06) | 0.12 | 100.97 |
| 9 M - 25° C. ± 2° C./40% ± 5% RH | * | ** | <A | 4.57 | 0.002 | ND | 0.035 (RRT-0.8) 0.034 (RRT-3.61) 0.025 (RRT-0.54) 0.007 (RRT-1.2) | 0.103 | 99.49 |
| 12 M - 25° C. ± 2° C./40% ± 5% RH | * | ** | <A | 4.58 | 0.007 | ND | 0.084 (RRT-0.79) 0.054 (RRT-0.53) 0.021 (RRT-1.21) | 0.233 | 102.42 |

* A clear and colorless solution filled in a bag
** Clear solution essentially free from visible particulate matter.
<A: Color of the solution is less intense than USP matching fluid A.
ND: Not detected

TABLE 19

Stability data for a premix formulation with 0.16 mg/ml phenylephrine HCl without SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial Autoclaved | * | ** | <A | 4.58 | ND | ND | ND | ND | 101.02 |

TABLE 19-continued

Stability data for a premix formulation with 0.16 mg/ml phenylephrine HCl without SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| 1 M - 40 °C. ± 2° C./NMT 25% RH | * | ** | <A | 4.58 | ND | ND | ND | ND | 102.4 |
| 2 M - 40° C. ± 2° C./NMT 25% RH | * | ** | <A | 4.54 | 0.003 | ND | 0.031 (RRT-3.98) | 0.083 | 100.9 |
| 3 M - 40° C. ± 2° C./NMT 25% RH | * | ** | <A | 4.57 | 0.004 | 0.009 | 0.021 (RRT-4.03) | 0.091 | 102.0 |
| 6 M - 40° C. ± 2° C./NMT 25% RH | * | ** | <A | 4.63 | ND | ND | 0.044 (RRT-2.52) | 0.087 | 98.8 |
| 1 M - 25° C. ± 2° C./40% ± 5% RH | * | ** | <A | 4.58 | ND | ND | ND | ND | 102.1 |
| 2 M - 25° C. ± 2° C./40% ± 5% RH | * | ** | <A | 4.56 | 0.002 | 0.023 | 0.007 (RRT-1.22) | 0.044 | 101.0 |
| 3 M - 25° C. ± 2° C./40% ± 5% RH | * | ** | <A | 4.58 | 0.002 | 0.018 | 0.007 (RRT-2.37) | 0.038 | 102.2 |
| 9 M - 25° C. ± 2° C./40% ± 5% RH | * | ** | <A | 4.63 | 0.002 | ND | 0.021 (RRT-0.8) 0.009 (RRT-0.54) 0.008 (RRT-1.2) | 0.04 | 99.9 |
| 12 M - 25° C. ± 2° C./40% ± 5% RH | * | ** | <A | 4.63 | 0.005 | ND | 0.100 (RRT-3.97) 0.032 (RRT-1.21) | 0.19 | 101.7 |

* A clear and colorless solution filled in a bag
** Clear solution essentially free from visible particulate matter.
<A: Color of the solution is less intense than USP matching fluid A.
ND: Not detected

TABLE 20

Stability data for a premix formulation with 0.4 mg/ml phenylephrine HCl without SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial Autoclaved | * | ** | <A | 4.43 | ND | ND | ND | ND | 101.42 |
| 1 M - 40° C. ± 2° C./NMT 25% RH | * | ** | <A | 4.47 | ND | ND | ND | ND | 100.92 |
| 2 M - 40° C. ± 2° C./NMT 25% RH | * | ** | <A | 4.48 | 0.008 | ND | 0.062 (RRT-0.52) 0.038 (RRT-4.08) | 0.145 | 101.81 |
| 3 M - 40° C. ± 2° C./NMT 25% RH | * | ** | <A | 4.53 | 0.008 | ND | 0.059 (RRT-0.52) 0.047 (RRT-4.09) | 0.158 | 101.56 |

TABLE 20-continued

Stability data for a premix formulation with 0.4 mg/ml phenylephrine HCl without SMBS and without oxygen scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| 1 M - 25° C. ± 2° C./40% ± 5% RH | * | ** | <A | 4.53 | ND | ND | ND | ND | 101.19 |
| 2 M - 25° C. ± 2° C./40% ± 5% RH | * | ** | <A | 4.50 | 0.002 | ND | 0.008 (RRT-052) 0.028 (RRT-4.04) | 0.054 | 101.02 |
| 3 M - 25° C. ± 2° C./40% ± 5% RH | * | ** | <A | 4.55 | 0.002 | ND | 0.016 (RRT-0.74) 0.019 (RRT-2.93) | 0.057 | 101.77 |
| 6 M - 25° C. ± 2° C./40% ± 5% RH | * | ** | <A | 4.57 | ND | ND | 0.024 (RRT-0.053) | 0.024 | 100.5 |
| 9 M - 25° C. ± 2° C./40% ± 5% RH | * | ** | <A | 4.61 | ND | ND | 0.024 (RRT-0.8) | 0.036 | 100.7 |
| 12 M - 25° C. ± 2° C./40% ± 5% RH | * | ** | <A | 4.54 | ND | ND | 0.025 (RRT-0.53) | 0.094 | 103.5 |

* A clear and colorless solution filled in a bag
** Clear solution essentially free from visible particulate matter.
<A: Color of the solution is less intense than USP matching fluid A.
ND: Not detected

Example 3: Sterilization of Premix Phenylephrine Formulation

The following example describes experiments evaluating the method of sterilization and also whether oxygen scavengers and SMBS provided stability for premix phenylephrine formulations.

Tables 21 and 22 provide data for a phenylephrine HCl formulation in an unautoclaved bag (aseptic) with SMBS and without or with an oxygen scavenger, respectively. Tables 23 and 24 provide data for a phenylephrine HCl formulation in an autoclaved bag (terminal sterilization) with SMBS and without or with an oxygen scavenger, respectively. All experiments in Tables 21-24 were performed using a premix phenylephrine HCl formulation containing 0.2 mg/mL phenylephrine HCl in 0.9% sodium chloride. Additional data using a premix phenylephrine HCl formulation containing 0.08 mg/mL phenylephrine HCl in 0.9% sodium chloride with or without oxygen scavengers is also provided in Tables 25 and 26.

The stability data described in Tables 21 and 22 indicated that the premix phenylephrine formulation is stable in either aseptic or terminal sterilization method when the formulation contained SMBS. The data in Tables 21 and 22 also show that the presence or absence of oxygen scavengers does not affect stability of the premix phenylephrine formulation with SMBS.

TABLE 21

Stability data for premix formulation with 0.2 mg/ml phenylephrine HCl w/SMBS and w/o oxygen scavengers-aseptic sterilization

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| Initial | * | ** | <A | 4.14 | 0.106 | ND | 0.088 (RRT-2.49) 0.027 (RRT-2.66) | 0.245 | 101.26 | No method |

TABLE 21-continued

Stability data for premix formulation with 0.2 mg/ml phenylephrine HCl w/SMBS and w/o oxygen scavengers-aseptic sterilization

| Condition (Time point/ Temper-ature/ Relative Humidity) | Descrip-tion A clear and colorless solution filled in a bag | Clarity of solution Clear solution essentially free from visible particulate matter. | Color and achromicity of solution Color of the solution should not be more intense than purified water | pH Between 3.0 and 6.5 | Phenyl-ephrone (phenyl-ephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Meta-bisulfite |
|---|---|---|---|---|---|---|---|---|---|---|
| 1 M - 40° C. ± 2° C./NMT 25% RH | * | ** | <A | 4.27 | 0.178 | ND | 0.122 (RRT-2.40) 0.089 (RRT-0.50) | 0.462 | 100.95 | No method |
| 2 M - 40° C. ± 2° C./NMT 25% RH | * | ** | <A | 4.41 | 0.216 | ND | 0.103 (RRT-0.50) 0.057 (RRT-0.53) | 0.390 | 101.18 | No method |
| 3 M - 40° C. ± 2° C./NMT 25% RH | * | ** | <A | 4.32 | 0.231 | ND | 0.146 (RRT-2.34) 0.107 (RRT-0.50) 0.067 (RRT-0.53) | 0.569 | 100.46 | ND |
| 6 M - 40° C. ± 2° C./NMT 25% RH | * | ** | <A | 4.13 | 0.228 | ND | 0.119 (RRT-0.40) 0.074 (RRT-0.48) 0.064 (RRT-0.53) 0.060 (RRT-3.33) 0.042 (RRT-0.57) | 0.587 | 98.34 | 2.31 |
| 3 M - 25° C. ± 2° C./40% ± 5% RH | * | ** | <A | 4.13 | 0.117 | ND | 0.105 (RRT-2.34) 0.082 (RRT-0.50) | 0.336 | 101.46 | ND |
| 6 M - 25° C. ± 2° C./40% ± 5% RH | * | ** | <A | 4.28 | 0.183 | ND | 0.131 (RRT-0.44) 0.110 (RRT-0.48) | 0.424 | 99.76 | ND |

* A clear and colorless solution filled in a bag
** Clear solution essentially free from visible particulate matter
<A: Color of the solution is less intense than USP matching fluid A.
ND: Not detected

TABLE 22

Stability data for a premix formulation with 0.2 mg/ml phenylephrine HCl with SMBS and with Oxygen Scavengers-Aseptic sterilization

| Condition (Time point/ Temper-ature/ Relative Humidity) | Descrip-tion A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Meta-bisulfite |
|---|---|---|---|---|---|---|---|---|---|---|
| Initial[#] | * | ** | <A | 4.14 | 0.106 | ND | 0.088 (RRT-2.49) 0.027 (RRT-2.66) | 0.245 | 101.26 | No method |

TABLE 22-continued

Stability data for a premix formulation with 0.2 mg/ml phenylephrine HCl with SMBS and with Oxygen Scavengers-Aseptic sterilization

| Condition (Time point/ Temper-ature/ Relative Humidity) | Descrip-tion A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Meta-bisulfite |
|---|---|---|---|---|---|---|---|---|---|---|
| 6 M - 40° C. ± 2° C./NMT 25% RH | * | ** | <A | 4.19 | 0.123 | ND | 0.076 (RRT-0.44) 0.069 (RRT-0.48) 0.046 (RRT-0.53) | 0.314 | 100.91 | 7.7 |
| 6 M - 25° C. ± 2° C./40% ± 5% RH | * | ** | <A | 4.20 | 0.052 | ND | 0.036 (RRT-0.44) | 0.088 | 100.28 | 33.44 |

* A clear and colorless solution filled in a bag
** Clear solution essentially free from visible particulate matter.
<A: Color of the solution is less intense than USP matching fluid A.
ND: Not detected

TABLE 23

Stability data for a premix formulation with 0.2 mg/ml phenylephrine HCl with SMBS and without oxygen scavengers-Terminal sterilization

| Condition (Time point/ Temperature/ Relative Humidity) | De-scription A clear and colorless solution filled in a bag | Clarity of solution Clear solution essentially free from visible particulate matter. | Color and achromicity of solution Color of the solution should not be more intense than purified water | pH Between 3.0 and 6.5 | Phenyl-ephrone (phenyl-ephrine related compound C) Not More Than 0.7% | Phenyl-ephrine-citrate adduct Not more than 0.4% | Any unspecified degradation product Not More Than 0.2% | Total degra-dation products Not More Than 1.3% | Assay of Phenylephrine HCl Between 90.0% and 115.0% of the label claim of Phenylephrine Hydrochloride | Assay of Sodium Meta-bisulfite |
|---|---|---|---|---|---|---|---|---|---|---|
| Initial Autoclaved | * | ** | <A | 4.04 | 0.174 | ND | 0.071 (RRT-3.26) 0.049 (RRT-2.45) | 0.304 | 101.54 | No method |
| 1 M - 40° C. ± 2° C./ NMT 25% RH | * | ** | <A | 4.00 | 0.197 | ND | 0.053 (RRT-2.41) 0.050 (RRT-0.53) | 0.381 | 101.15 | No method |
| 2 M - 40° C. ± 2° C./ NMT 25% RH | * | ** | <A | 3.96 | 0.193 | ND | 0.049 (RRT-0.53) 0.048 (RRT-0.51) | 0.326 | 100.95 | No method |
| 3 M - 40° C. ± 2° C./ NMT 25% RH | * | ** | <A | 3.95 | 0.187 | ND | 0.044 (RRT-0.53) 0.042 (RRT-0.50) 0.038 (RRT-2.34) | 0.322 | 101.18 | ND |
| 6 M - 40° C. ± 2° C./ NMT 25% RH | * | ** | <A | 3.91 | 0.138 | ND | 0.049 (RRT-3.33) 0.045 (RRT-0.44) 0.042 (RRT-0.53) | 0.274 | 99.43 | 2.7 |
| 3 M - 25° C. ± 2° C./ 40% ± 5% RH | * | ** | <A | 4.04 | 0.169 | ND | 0.054 (RRT-0.50) 0.038 (RRT-2.34) 0.041 (RRT-0.53) | 0.362 | 100.73 | ND |
| 6 M - 25° C. ± 2° C./ 40% ± 5% RH | * | ** | <A | 4.13 | 0.196 | ND | 0.075 (RRT-0.44) 0.055 (RRT-0.48) 0.040 (RRT-0.53) | 0.366 | 99.52 | ND |

* A clear and colorless solution filled in a bag
** Clear solution essentially free from visible particulate matter.
<A: Color of the solution is less intense than USP matching fluid A.
ND: Not detected

TABLE 24

Stability data for a premix formulation with 0.2 mg/ml phenylephrine HCl with SMBS and with oxygen scavengers-Terminal sterilization

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Meta-bisulfite |
|---|---|---|---|---|---|---|---|---|---|---|
| 6 M - 40° C. ± 2° C./ NMT 25% RH | *• | *•*• | <A | 4.20 | 0.176 | ND | 0.061 (RRT-0.44)<br>0.049 (RRT-0.48)<br>0.043 (RRT-0.53) | 0.329 | 99.71 | 7.07 |
| 6 M - 25° C. ± 2° C./ 40% ± 5% RH | * | ** | <A | 4.17 | 0.169 | ND | 0.053 (RRT-0.44)<br>0.045 (RRT-0.48)<br>0.036 (RRT-0.53)<br>0.035 (RRT-2.95) | 0.338 | 100.27 | ND |

* A clear and colorless solution filled in a bag
** Clear solution essentially free from visible particulate matter.
<A: Color of the solution is less intense than USP matching fluid A.
ND: Not detected The phenylephrine HCl injection 0.2 mg/mL in 0.9% sodium chloride containing SMBS with or without an oxygen scavenger was stable under either the aseptic or terminal sterilization method.

TABLE 25

Stability of sterilized premix formulation (0.08 mg/ml phenylephrine HCl) with SMBS and without oxygen scavengers-Terminal sterilization

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Meta-bisulfite |
|---|---|---|---|---|---|---|---|---|---|---|
| Initial | * | ** | <A | 3.63 | 0.232 | ND | 0.114 (RRT-0.46)<br>0.080 (RRT-0.50)<br>0.064 (RRT-0.54) | 0.538 | 100.58 | 28.73 |
| 1 M - 40° C. ± 2° C./ NMT 25% RH | * | ** | <A | 3.48 | 0.326 | ND | 0.143 (RRT-0.41)<br>0.116 (RRT-0.45)<br>0.103 (RRT-0.52) | 0.717 | 99.29 | ND |
| 2 M - 40° C. ± 2° C./ NMT 25% RH | *• | ** | <A | 3.48 | 0.304 | ND | 0.163 (RRT-0.42)<br>0.124 (RRT-3.28)<br>0.113 (RRT-0.47)<br>0.071 (RRT-0.51)<br>0.067 (RRT-2.22) | 0.842 | 100.59 | ND |
| 3 M - 40° ± 2° C./ NMT 25% RH | * | ** | <A | 3.51 | 0.343 | ND | 0.169 (RRT-0.46)<br>0.090 (RRT-0.53)<br>0.088 (RRT-0.51)<br>0.065 (RRT-2.48) | 0.755 | 100.50 | ND |
| 6 M - 40° C. ± 2° C./ NMT 25% RH | * | ** | <A | 3.51 | 0.269 | 0.026 | 0.148 (RRT-3.33)<br>0.077 (RRT-0.43)<br>0.053 (RRT-0.47)<br>0.081 (RRT-0.52) | 0.861 | 101.05 | ND |
| 1 M - 25° C. ± 2° C./ 40% ± 5% RH | * | ** | <A | 3.55 | 0.294 | ND | 0.105 (RRT-0.45)<br>0.098 (RRT-0.41)<br>0.087 (RRT-0.52) | 0.601 | 99.45 | 19.8 |

TABLE 25-continued

Stability of sterilized premix formulation (0.08 mg/ml phenylephrine HCl) with SMBS and without oxygen scavengers-Terminal sterilization

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| 2 M - 25° C. ± 2° C./ 40% ± 5% RH | * | ** | <A | 3.56 | 0.209 | ND | 0.128 (RRT-0.42)<br>0.125 (RRT-3.27)<br>0.102 (RRT-0.47)<br>0.059 (RRT-2.22) | 0.623 | 100.82 | 14.44 |
| 3 M - 25° C. ± 2° C./ 40% ± 5% RH | * | ** | <A | 3.69 | 0.245 | ND | 0.136 (RRT-0.46)<br>0.070 (RRT-2.48) | 0.451 | 100.59 | 15.94 |
| 6 M - 25° C ± 2° C./ 40% ± 5% RH | * | ** | <A | 3.67 | 0.253 | ND | 0.111 (RRT-0.47)<br>0.107 (RRT-0.43)<br>0.089 (RRT-2.24) | 0.669 | 101.31 | 15.84 |
| 12 M - 25° C. ± 2° C./ 40% ± 5% RH | * | ** | <A | 3.53 | 0.139 | ND | 0.073 (RRT-0.48)<br>0.071 (RRT-3.77)<br>0.042 (RRT-0.52)<br>0.043 (RRT-3.85) | 0.504 | 100.2 | 3.34 |

* A clear and colorless solution filled in a bag
** Clear solution essentially free from visible particulate matter.
<A: Color of the solution is less intense than USP matching fluid A.
ND = not detected

TABLE 26

Stability data for a terminally sterilized premix formulation with 0.08 mg/ml phenylephrine HCl with SMBS and with oxygen scavengers-Terminal sterilization

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| 6 M - 40° C. ± 2° C./ NMT 25% RH | * | ** | <A | 4.07 | 0.146 | ND | 0.144 (RRT-3.33)<br>0.040 (RRT-0.43) | 0.424 | 102.40 | 46.3 |

* A clear and colorless solution filled in a bag
** Clear solution essentially free from visible particulate matter.
<A: Color of the solution is less intense than USP matching fluid A.
ND = not detected The Phenylephrine Hydrochloride injection 0.08 mg/mL in 0.9% sodium chloride containing SMBS with or without an oxygen scavenger was stable under the terminal sterilization method.

Example 4: Impact of SMBS on Photostability

The impact of SMBS on premix phenylephrine formulations was tested, all in the absence of oxygen scavengers. The experiment was performed using a premix phenylephrine formulation containing 0.08 mg/mL phenylephrine HCl in 0.9% sodium chloride, with or without SMBS. Results are provided in Tables 27 to 29. The data indicated that the premix phenylephrine formulation was stable. The formulations were tested in a commercial pack having one side amber and one side aluminum (alu) overpouch.

TABLE 27

Photostability data for a terminally sterilized premix formulation with 0.08 mg/ml phenylephrine HCl with SMBS and without Oxygen Scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| Naked Sample (Without Overpouch) | * | ** | <A | 3.49 | 0.445 | ND | 0.304 (RRT-0.52)<br>0.144 (RRT-3.28) | 0.893 | 97.23 | ND |
| Clear Alu. Overpouch | * | ** | <A | 3.59 | 0.285 | ND | 0.208 (RRT-0.42)<br>0.148 (RRT-0.47)<br>0.123 (RRT-3.27)<br>0.082 (RRT-2.22)<br>0.070 (RRT-0.52) | 0.916 | 100.36 | 19.08 |
| Amber Alu. Overpouch | * | ** | <A | 3.55 | 0.231 | ND | 0.155 (RRT-0.42)<br>0.124 (RRT-3.27)<br>0.110 (RRT-0.47)<br>0.064 (RRT-2.22) | 0.684 | 100.56 | 12.81 |
| Control Sample Amber Alu. Overpouch Control sample | * | ** | <A | 3.54 | 0.229 | ND | 0.138 (RRT-0.42)<br>0.124 (RRT-3.27)<br>0.110 (RRT-0.47)<br>0.062 (RRT-2.23) | 0.663 | 100.60 | 13.66 |

* A clear and colorless solution filled in a bag
** Clear solution essentially free from visible particulate matter.
<A: Color of the solution is less intense than USP matching fluid A.
ND = not detected

TABLE 28

Photostability data for a terminally sterilized premix formulation with 0.08 mg/ml phenylephrine HCl without SMBS and without Oxygen Scavengers

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride | Assay of Sodium Metabisulfite |
|---|---|---|---|---|---|---|---|---|---|---|
| Initial | *• | ** | <A | 3.63 | 0.232 | ND | 0.114 (RRT-0.46)<br>0.080 (RRT-0.50)<br>0.064 (RRT-0.54) | 0.538 | 100.58 | 28.73 |
| Clear Aluminum Overpouch 1M Day light PHE/US/I-20/001A | * | ** | <A | 3.52 | 0.416 | ND | 0.206 (RRT-0.42)<br>0.155 (RRT-0.47)<br>0.123 (RRT-3.27)<br>0.104 (RRT-2.22)<br>0.050 (RRT-0.52) | 1.054 | 99.92 | 10.41 |
| Amber Alu. Overpouch 1 M Day light PHE/US/I-20/001B | * | ** | <A | 3.58 | 0.197 | ND | 0.131 (RRT-0.42)<br>0.121 (RRT-3.27)<br>0.101 (RRT-0.47)<br>0.058 (RRT-2.22) | 0.608 | 100.87 | 19.12 |

* A clear and colorless solution filled in a bag
** Clear solution essentially free from visible particulate matter.
<A: Color of the solution is less intense than USP matching fluid A.
ND = not detected The terminally sterilized phenylephrine hydrochloride injection 0.08 mg/mL in 0.9% sodium chloride without oxygen scavengers and with or without SMBS, was stable in the pack of one side amber & another side aluminum overpouch.

TABLE 29

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Photostability data for premix formulation with 0.1 mg/ml phenylephrine HCl without SMBS and without Oxygen Scavengers | | | | | | | | | |
| Initial Autoclaved sample | * | ** | <A | 4.54 | ND | ND | ND | ND | 98.90 |
| Naked Sample Without Overpouch | *• | ** | <A | 4.55 | 0.016 | ND | 1.370 (RRT-0.52)<br>0.235 (RRT-1.46)<br>0.101 (RRT-0.64)<br>0.053 (RRT-2.25) | 1.775 | 93.58 |
| Clear Alu. Overpouch Marketed Pack | *• | ** | <A | 4.62 | 0.034 | ND | 1.746 (RRT-0.52)<br>0.228 (RRT-0.64)<br>0.116 (RRT-1.46)<br>0.071 (RRT-2.24) | 2.195 | 93.21 |
| Amber Alu. Overpouch Marketed Pack | * | ** | <A | 4.56 | ND | ND | 0.082 (RRT-0.52) | 0.082 | 100.26 |
| Control Sample Amber Alu. Overpouch Control sample | *• | ** | <A | 4.53 | ND | ND | ND | ND | 100.69 |

* A clear and colorless solution filled in a bag
** Clear solution essentially free from visible particulate matter.
<A: Color of the solution is less intense than USP matching fluid A.
ND = not detected The phenylephrine hydrochloride injection 0.1 mg/mL in 0.9% sodium chloride was also stable in the pack of one side amber & another side aluminum over pouch.

Example 5: Testing of Impact of Oxygen Scavengers on Premix Phenylephrine HCl Formulations The following example provides experiments that evaluated the stability of premix phenylephrine formulations with and without an oxygen scavenger. The formulations did not contain SMBS. The data is provided in Tables 30-33.

With respect to Tables 30 and 31, the stability data for phenylephrine hydrochloride injection 0.1 mg/mL in 0.9% sodium chloride that did not contain SMBS revealed that the formulation is relatively stable in the presence of oxygen scavenger (Table 31) and relatively less stable without a scavenger and without SMBS (Table 30)—noting that there were no significant differences observed across all of the trials.

TABLE 30

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenylephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Phenylephrine HCl injection 0.1 mg/ml in 0.9% NaCl; without SMBS and without oxygen scavenger | | | | | | | | | |
| Initial Autoclaved | * | ** | <A | 4.54 | ND | ND | ND | ND | 98.90 |
| 1 M - 40° C. ± 2° C./ NMT 25% RH | * | ** | <A | 4.53 | ND | ND | ND | ND | 100.72 |
| 2 M - 40° C. ± 2° C./ NMT 25% RH | * | ** | <A | 4.49 | 0.005 | 0.025 | 0.077 (RRT-0.52)<br>0.064 (RRT-4.06) | 0.275 | 101.04 |
| 3 M - 40° C. ± 2° C./ NMT 25% RH | * | ** | <A | 4.53 | 0.006 | 0.027 | 0.108 (RRT-0.52)<br>0.048 (RRT-4.03) | 0.282 | 100.96 |
| 6 M - 40° C. ± 2° C./ NMT 25% RH | * | ** | <A | 4.55 | ND | ND | 0.285 (RRT-4.41)<br>0.130 (RRT-3.35)<br>0.080 (RRT-4.67) | 1.197 | 97.2 |

TABLE 30-continued

Phenylephrine HCl injection 0.1 mg/ml in 0.9% NaCl; without SMBS and without oxygen scavenger

| Condition (Time point/ Temperature/ Relative Humidity) | De-scription A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degra-dation products Not More Than 1.3% | Assay of Phenylephrine HCl Between 90.0% and 115.0% of the label claim of Phenylephrine Hydrochloride |
|---|---|---|---|---|---|---|---|---|---|
| 1 M - 25° C. ± 2° C./ 40% ± 5% RH | * | ** | <A | 4.54 | ND | ND | ND | ND | 100.5 |
| 2 M - 25° C. ± 2° C./ 40% ± 5% RH | * | ** | <A | 4.52 | 0.003 | ND | 0.025 (RRT-0.52)<br>0.025 (RRT-3.37) | 0.109 | 101.12 |
| 3 M - 25° C. ± 2° C./ 40% ± 5% RH | * | ** | <A | 4.54 | 0.003 | ND | 0.022 (RRT-0.52)<br>0.030 (RRT-4.06) | 0.12 | 100.97 |
| 9 M - 25° C. ± 2° C./ 40% ± 5% RH | * | ** | <A | 4.57 | 0.002 | ND | 0.035 (RRT-0.8)<br>0.034 (RRT-3.61)<br>0.025 (RRT-0.54)<br>0.007 (RRT-1.2) | 0.103 | 99.49 |
| 12 M - 25° C. ± 2° C./40% ± 5% RH | * | ** | <A | 4.58 | 0.007 | ND | 0.084 (RRT-0.79)<br>0.054 (RRT-0.53)<br>0.021 (RRT-1.21) | 0.233 | 102.42 |

* A clear and colorless solution filled in a bag
** Clear solution essentially free from visible particulate matter.
<A: Color of the solution is less intense than USP matching fluid A.
ND—not detectable

TABLE 31

Phenylephrine HCl injection 0.1 mg/ml in 0.9% NaCl; without SMBS and with oxygen scavenger

| Condition (Time point/ Temperature/ Relative Humidity) | De-scription A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degra-dation products Not More Than 1.3% | Assay of Phenylephrine HCl Between 90.0% and 115.0% of the label claim of Phenylephrine Hydrochloride |
|---|---|---|---|---|---|---|---|---|---|
| Initial Autoclaved | * | ** | <A | 4.53 | ND | ND | ND | ND | 100.7 |
| 1 M - 40° C. ± 2° C./ NMT 25% RH | * | ** | <A | 4.53 | ND | ND | ND | ND | 100.6 |
| 2 M - 40° C. ± 2° C./ NMT 25% RH | * | ** | <A | 4.53 | 0.004 | ND | 0.030 (RRT-3.37)<br>0.027 (RRT-0.52) | 0.138 | 101.1 |
| 3 M - 40° C. ± 2° C./ NMT 25% RH | * | ** | <A | 4.56 | 0.005 | 0.016 | 0.053 (RRT-0.52)<br>0.045 (RRT-4.08) | 0.215 | 101.1 |
| 6 M - 40° C. ± 2° C./ NMT 25% RH | * | ** | <A | 4.62 | ND | ND | 0.074 (RRT-1.2)<br>0.062 (RRT-4.41)<br>0.062 (RRT-3.48) | 0.323 | 100.2 |
| 1 M - 25° C. ± 2° C./ 40% ± 5% RH | * | ** | <A | 4.54 | ND | ND | ND | ND | 100.3 |
| 2 M - 25° C. ± 2° C./ 40% ± 5% RH | * | ** | <A | 4.53 | 0.002 | ND | 0.029 (RRT-0.52)<br>0.026 (RRT-3.37) | 0.093 | 101.2 |
| 3 M - 25° C. ± 2° C./ 40% ± 5% RH | * | ** | <A | 4.55 | 0.002 | ND | 0.029 (RRT-0.52)<br>0.027 (RRT-3.37) | 0.091 | 101.2 |
| 9 M - 25° C. ± 2° C./ 40% ± 5% RH | * | ** | <A | 4.61 | 0.002 | ND | 0.0329 RRT-3.61)<br>0.023 (RRT-0.8)<br>0.009 (RRT-0.54) | 0.066 | 98.9 |
| 12 M - 25° C. ± 2° C./40% ± 5% RH | * | ** | <A | 4.63 | 0.006 | ND | 0.044 (RRT-0.79)<br>0.022 (RRT-1.54) | 0.145 | 102.86 |

* A clean and colorless solution filled in a bag
** Clear solution essentially free from visible particulate matter.
<A: Color of the solution is less intense than USP matching fluid A.
ND—not detectable

TABLE 32

Phenylephrine HCl injection 0.16 mg/ml in 0.9% NaCl; without SMBS and without oxygen scavenger

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial Autoclaved | * | ** | <A | 4.58 | ND | ND | 0.090 | 0.090 | 101.02 |
| 1 M - 40° C. ± 2° C./ NMT 25% RH | * | ** | <A | 4.58 | ND | ND | ND | ND | 102.35 |
| 2 M - 40° C. ± 2° C./ NMT 25% RH | * | ** | <A | 4.54 | 0.003 | ND | 0.031 (RRT-3.98) | 0.083 | 100.92 |
| 3 M - 40° C. ± 2° C./ NMT 25% RH | * | ** | <A | 4.57 | 0.004 | 0.009 | 0.021 (RRT-4.03) | 0.091 | 102.0 |
| 6 M - 40° C. ± 2° C./ NMT 25% RH | * | ** | <A | 4.63 | ND | ND | 0.044 (RRT-2.52) | 0.244 | 98.8 |
| 1 M - 25° C. ± 2° C./ 40% ± 5% RH | * | ** | <A | 4.58 | ND | ND | ND | ND | 102.14 |
| 2 M - 25° C. ± 2° C./ 40% ± 5% RH | * | ** | <A | 4.56 | 0.002 | 0.023 | 0.007 (RRT-1.22) | 0.044 | 100.96 |
| 3 M - 25 C ± 2 C./ 40% ± 5% RH | * | ** | <A | 4.58 | 0.002 | 0.018 | 0.007 (RRT-2.37) | 0.038 | 102.19 |
| 9 M - 25° C. ± 2° C./ 40% ± 5% RH | * | ** | <A | 4.63 | 0.002 | ND | 0.021 (RRT-0.8) 0.009 (RRT-0.54) 0.008 (RRT-1.2) | 0.04 | 99.9 |
| 12 M- 25° C. ± 2° C./ 40% ± 5% RH | * | ** | <A | 4.63 | 0.005 | ND | 0.100 (RRT-3.97) 0.032 (RRT-1.21) | 0.19 | 101.7 |

* A clear and colorless solution filled in a bag
** Clear solution essentially free from visible particulate matter.
<A: Color of the solution is less intense than USP matching fluid A.
ND—not detectable

TABLE 33

Phenylephrine HCl injection 0.16 mg/ml in 0.9% NaCl; without SMBS and with oxygen scavenger

| Condition (Time point/ Temperature/ Relative Humidity) | Description A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degradation products Not More Than 1.3% | Assay of Phenylephrine HCl Between 90.0% and 115.0% of the label claim of Phenylephrine Hydrochloride |
|---|---|---|---|---|---|---|---|---|---|
| Initial Autoclaved | * | ** | <A | 4.58 | ND | ND | 0.092 | 0.092 | 101.32 |
| 1 M - 40° C. ± 2° C./ NMT 25% RH | * | ** | <A | 4.60 | ND | ND | ND | ND | 101.98 |
| 2 M - 40° C. ± 2° C./ NMT 25% RH | * | ** | <A | 4.59 | 0.003 | 0.005 | 0.013 (RRT-2.37) | 0.063 | 101.4 |
| 3 M - 40° C. ± 2° C./ NMT 25% RH | * | ** | <A | 4.62 | 0.003 | ND | 0.013 (RRT-1.22) | 0.041 | 101.39 |
| 6 M - 40° C. ± 2° C./ NMT 25% RH | * | ** | <A | 4.64 | ND | ND | 0.043 (RRT-2.52) | 0.095 | 98.9 |
| 1 M - 25° C. ± 2° C./ 40% ± 5% RH | * | ** | <A | 4.59 | ND | ND | ND | ND | 101.97 |
| 2 M - 25° C. ± 2° C./ 40% ± 5% RH | * | ** | <A | 4.57 | 0.002 | 0.02 | 0.005 (RRT-1.22) | 0.032 | 100.74 |
| 3 M - 25° C. ± 2° C./ 40% ± 5% RH | * | ** | <A | 4.59 | 0.002 | 0.015 | 0.007 (RRT-2.37) | 0.039 | 101.22 |
| 9 M - 25° C. ± 2° C./ 40% ± 5% RH | * | ** | <A | 4.66 | ND | ND | 0.016 (RRT-0.8) 0.006 (RRT-1.2) | 0.022 | 100.3 |

TABLE 33-continued

| Phenylephrine HCl injection 0.16 mg/ml in 0.9% NaCl; without SMBS and with oxygen scavenger | | | | | | | | | |
|---|---|---|---|---|---|---|---|---|---|
| Condition (Time point/ Temperature/ Relative Humidity) | De-scription A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degra-dation products Not More Than 1.3% | Assay of Phenylephrine HCl Between 90.0% and 115.0% of the label claim of Phenylephrine Hydrochloride |
| 12 M - 25° C. ± 2° 4C./0% ± 5% RH | * | ** | <A | 4.66 | ND | ND | 0.090 (RRT-3.99) 0.027 (RRT-1.21) | 0.143 | 101.4 |

* A clear and colorless solution filled in a bag
** Clear solution essentially free from visible particulate matter.
<A: Color of the solution is less intense than USP matching fluid A.
ND—not detectable The stability data revealed that the liquid premix phenylephrine HCl formulation with 0.1 mg/mL or 0.16 mg/mL phenylephrine HCl was stable in the presence of oxygen scavenger and comparable or relatively less stable without oxygen scavenger.

Example 6: Analysis of Buffer Free Formulation

Table 34 below provides stability data for a phenylephrine HCl premix formulation with no SMBS and no buffer. An oxygen scavenger was used with the formulation. The conclusion of the stability data provided in Table 34 was that the formulation is stable in the absence of a buffer also in the formulation.

TABLE 34

| Phenylephrine HCl Injection, 0.08 mg/mL - Batch without SMBS & without Buffer, with Oxygen scavenger | | | | | | | | | |
|---|---|---|---|---|---|---|---|---|---|
| Condition (Time point/ Temperature/ Relative Humidity) | De-scription A clear and colorless solution filled in a bag | Clarity of solution Clear solution essentially free from visible particulate matter. | Color and achromicity of solution Color of the solution should not be more intense than purified water | pH Between 3.0 and 6.5 | Phenylephrone (phenylephrine related compound C) Not More Than 0.7% | Phenyl-ephrine-citrate adduct Not more than 0.4% | Any unspecified degradation product Not More Than 0.2% | Total degra-dation products Not More Than 1.3% | Assay of Phenylephrine HCl Between 90.0% and 115.0% of the label claim of Phenylephrine Hydrochloride |
| Initial | * | ** | <A | 4.72 | ND | ND | ND | ND | 101.1 |
| 1 M - 40° C. ± 2° C./ NMT 25% RH | * | ** | <A | 4.8 | 0.004 | ND | 0.016 (RRT-4.37) 0.007 (RRT-1.22) | 0.027 | 101.6 |
| 2 M - 40° C. ± 2° C./ NMT 25% RH | *• | ** | <A | 5.01 | 0.003 | ND | 0.019 (RRT-4.37) 0.016 (RRT-3.37) | 0.056 | 101.7 |
| 3 M- 40° C. ± 2° C./ NMT 25% RH | * | ** | <A | 5.12 | 0.003 | ND | 0.024 (RRT-4.37) | 0.074 | 101.7 |
| 6 M- 40° C. ± 2° C./ NMT 25% RH | * | ** | <A | 5.21 | ND | ND | 0.058 (RRT-3.66) | 0.113 | 101.4 |
| 1 M- 25° C. ± 2° C./ 40% ± 5% RH | * | ** | <A | 5.23 | 0.003 | ND | 0.019 (RRT-4.37) | 0.022 | 101.5 |
| 2 M- 25° C. ± 2° C./ 40% ± 5% RH | * | ** | <A | 4.88 | 0.003 | ND | 0.027 (RRT-3.37) | 0.049 | 101.2 |
| 3 M- 25° C. ± 2° C./ 40% ± 5% RH | * | ** | <A | 4.95 | 0.003 | ND | 0.029 (RRT-3.36) | 0.064 | 101.5 |
| 6 M- 25° C. ± 2° C./ 40% ± 5% RH | * | ** | <A | 5.03 | ND | ND | 0.063 (RRT-3.65) | 0.093 | 101.9 |
| 9 M 25° C. ± 2° C./ 40% ± 5% RH | * | ** | <A | 5.00 | ND | ND | 0.016 (RRT-0.79) | 0.022 | 100.4 |
| 12 M- 25° C. ± 2° C./ 40% ± 5% RH | * | ** | <A | 5.03 | 0.005 | ND | 0.035 (RRT-0.79) | 0.083 | 103.2 |

What is claimed:

1. A container comprising a pharmaceutical premix formulation comprising from about 0.05 mg/ml to about 0.4 mg/ml phenylephrine hydrochloride, about 8.5 mg/ml to about 9.5 mg/ml sodium chloride, and a buffer consisting of about 0.05 to about 1.1 mg/ml sodium citrate dihydrate and about 0.01 to about 0.03 mg/ml citric acid monohydrate,
   wherein the container is for intravenous administration,
   wherein the pharmaceutical premix formulation is an aqueous, premix formulation for intravenous administration and has a pH from about 3.0 to about 6.5,
   wherein the pharmaceutical premix formulation is stable at 25 degrees Celsius for at least 6 months, and
   wherein the pharmaceutical premix formulation is free of ethylenediaminetetraacetic acid (EDTA) and is free of sodium metabisulfite.

2. The container of claim 1, comprising from about 0.08 mg/ml to about 0.4 mg/ml phenylephrine hydrochloride.

3. The container of claim 1, comprising about 0.08 mg/ml phenylephrine hydrochloride.

4. The container of claim 1, comprising about 8.7 mg/ml to about 9.3 mg/ml sodium chloride; or about 9 mg/ml sodium chloride.

5. The container of claim 1, wherein the pH of the pharmaceutical premix formulation is from about 3.5 to about 6.0.

6. The container of claim 1, wherein the buffer consists of about 0.08 mg/ml sodium citrate dihydrate and about 0.02 mg/ml citric acid monohydrate.

7. The container of claim 1, wherein the formulation is antioxidant free.

8. A container comprising a pharmaceutical premix formulation consisting essentially of
   about 0.05 mg/ml to about 0.4 mg/ml phenylephrine hydrochloride,
   about 8.4 mg/ml to about 9.4 mg/ml sodium chloride,
   about 0.05 to about 1.1 mg/ml sodium citrate dihydrate, and
   about 0.01 to about 0.03 mg/ml citric acid monohydrate,
   wherein the container is for intravenous administration,
   wherein the pharmaceutical premix formulation is an aqueous, premix formulation for intravenous administration and has a pH from about 3.0 to about 6.5,
   wherein the pharmaceutical premix formulation is free of EDTA and is free of sodium metabisulfite, and
   wherein the pharmaceutical premix formulation is stable at 25 degrees Celsius for at least 6 months.

9. A container comprising a pharmaceutical premix formulation consisting essentially of
   phenylephrine hydrochloride,
   about 0.9% sodium chloride,
   about 0.08 mg/ml sodium citrate dihydrate, and
   about 0.02 mg/ml citric acid monohydrate,
   wherein the container is for intravenous administration,
   wherein the pharmaceutical premix formulation is an aqueous, premix formulation for intravenous administration, and has a pH from about 3.0 to about 6.5,
   wherein the concentration of phenylephrine hydrochloride is about 0.08 mg/ml to about 0.4 mg/ml,
   wherein the pharmaceutical premix formulation is stable at 25 degrees Celsius for at least 6 months, and
   wherein the pharmaceutical premix formulation is free of EDTA and is free of sodium metabisulfite.

10. The container of claim 9, wherein the container is a flexible container which is an intravenous bag.

11. The flexible container of claim 10, wherein the flexible container comprises multilayers of polypropylene (PP), polyamide (PA), polyethylene (PE), or a combination thereof.

12. The flexible container of claim 10, having a volume of about 100 mL or about 250 mL.

13. A system comprising an oxygen scavenger and the flexible container of claim 11.

14. A system comprising an oxygen scavenger and the flexible container of claim 10.

15. The system of claim 14, further comprising an overpouch which is photosensitive.

16. A system consisting essentially of an oxygen scavenger, a photosensitive overpouch, and the flexible container of claim 10.

17. The system of claim 16, wherein the oxygen scavenger is in a polyethylene flexible container.

18. The system of claim 16, wherein the oxygen scavenger comprises micronized iron.

19. The system of claim 16, wherein the oxygen scavenger is located in between a flexible container comprising the pharmaceutical premix formulation and the overpouch.

20. The container of claim 1, wherein the pharmaceutical premix formulation comprises about 0.1 mg/ml phenylephrine hydrochloride.

21. The container of claim 1, wherein the pharmaceutical premix formulation comprises about 0.16 mg/ml phenylephrine hydrochloride.

22. The container of claim 1, wherein the pharmaceutical premix formulation comprises about 0.2 mg/ml phenylephrine hydrochloride.

23. The container of claim 1, wherein the pharmaceutical premix formulation comprises about 0.4 mg/ml phenylephrine hydrochloride.

24. The container of claim 8, wherein the pharmaceutical premix formulation comprises about 0.08 mg/ml phenylephrine hydrochloride.

25. The container of claim 8, wherein the pharmaceutical premix formulation comprises about 0.1 mg/ml phenylephrine hydrochloride.

26. The container of claim 8, wherein the pharmaceutical premix formulation comprises about 0.16 mg/ml phenylephrine hydrochloride.

27. The container of claim 8, wherein the pharmaceutical premix formulation comprises about 0.2 mg/ml phenylephrine hydrochloride.

28. The container of claim 8, wherein the pharmaceutical premix formulation comprises about 0.4 mg/ml phenylephrine hydrochloride.

29. The container of claim 1, wherein the container is an intravenous bag.

30. The container of claim 8, wherein the container is an intravenous bag.

31. The container of claim 9, wherein the pharmaceutical premix formulation comprises about 0.08 mg/ml phenylephrine hydrochloride.

32. The container of claim 9, wherein the pharmaceutical premix formulation comprises about 0.1 mg/ml phenylephrine hydrochloride.

33. The container of claim 9, wherein the pharmaceutical premix formulation comprises about 0.16 mg/ml phenylephrine hydrochloride.

34. The container of claim 9, wherein the pharmaceutical premix formulation comprises about 0.2 mg/ml phenylephrine hydrochloride.

35. The container of claim 9, wherein the pharmaceutical premix formulation comprises about 0.4 mg/ml phenylephrine hydrochloride.

* * * * *